(12) United States Patent
Okada et al.

(10) Patent No.: US 7,694,864 B2
(45) Date of Patent: Apr. 13, 2010

(54) TISSUE STAPLER WITH POSITIONING MECHANISM

(75) Inventors: Yuta Okada, Tokyo (JP); Ryuta Sekine, Tokyo (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 12/436,402

(22) Filed: May 6, 2009

(65) Prior Publication Data

US 2009/0212088 A1    Aug. 27, 2009

Related U.S. Application Data

(63) Continuation of application No. 11/179,215, filed on Jul. 12, 2005, now abandoned.

(30) Foreign Application Priority Data

Apr. 22, 2009    (JP) ............................. 2004-207740

(51) Int. Cl.
 *A61B 17/04* (2006.01)
(52) U.S. Cl. ................. 227/175.1; 227/19; 227/179.1; 227/180.1
(58) Field of Classification Search .............. 227/175.1, 227/19, 180.1, 179.1
See application file for complete search history.

(56) References Cited

U.S. PATENT DOCUMENTS

| 5,445,644 | A | * | 8/1995 | Pietrafitta et al. | 606/151 |
| 5,474,223 | A | * | 12/1995 | Viola et al. | 227/179.1 |
| 5,533,661 | A | * | 7/1996 | Main et al. | 227/176.1 |
| 5,868,760 | A | * | 2/1999 | McGuckin, Jr. | 606/139 |
| 6,119,913 | A | * | 9/2000 | Adams et al. | 227/176.1 |
| 6,241,140 | B1 | * | 6/2001 | Adams et al. | 227/180.1 |
| 6,279,809 | B1 | * | 8/2001 | Nicolo | 227/176.1 |
| 6,302,311 | B1 | * | 10/2001 | Adams et al. | 227/176.1 |
| 2005/0119524 | A1 | * | 6/2005 | Sekine et al. | 600/114 |

\* cited by examiner

*Primary Examiner*—Brian D Nash
(74) *Attorney, Agent, or Firm*—Ostrolenk Faber LLP

(57) ABSTRACT

A position information transmitting member for transmitting position information to a staple receiving portion is provided in a tissue stapler having a staple receiving portion which comprises the anvil of the stapler. Thereby, an operator can easily locate the position of and grasp the staple receiving portion located within a tissue to swiftly execute stapling. The tissue stapler includes a stapling portion provided with an endoscope inserting tube path, a stapling portion provided with a staple injecting portion arranged on a distal end side of the inserting portion, and a staple receiving member (anvil) arranged separately from the inserting portion, to be grasped by a treatment tool introduced via the inserting portion in a state when it is opposed to the stapling portion via a tissue, to bend a distal end portion of a staple pressed out from the staple injecting portion of the stapling portion which has penetrated through the tissue.

16 Claims, 17 Drawing Sheets

TISSUE STAPLER WITH POSITIONING MECHANISM

CROSS-REFERENCE TO RELATED APPLICATIONS

The present application is a continuation of prior application Ser. No. 11/179,215, filed Jul. 12, 2005, by Yuta Okada and Ryuta Sekine, entitled TISSUE STAPLER WITH POSITIONING MECHANISM (now abandoned), which is based upon and claims the benefit of priority from prior Japanese Patent Application No. 2004-207740, filed Jul. 14, 2004, the entire contents of which are incorporated herein by reference.

BACKGROUND OF THE INVENTION

1. Field of the Invention

The present invention relates to a tissue stapling method and a tissue stapler. A tissue stapler is used when, for example, the intraluminal organ of the esophagus, the stomach or the like is subjected to an anastomosis or a fixing treatment during surgery or the like.

2. Description of the Related Art

Tissue staplers have been known in the related art. A tissue stapler is used in anastomosing end portions of the normal intraluminal organ after or before cutting off a morbid or diseased portion of the intraluminal organ of, for example, the large intestine, or the small intestine, or in anastomosing side portions of the stomach and the small intestines. Such a tissue stapler can considerably shorten an operation time period by stapling the tissue with a plurality of staples, arranged in a ring-like shape and simultaneously cutting off a substantially central portion of the tissue stapled along the ring-like shape.

Such a tissue stapler is provided with a stapling portion arranged with a plurality of staples at a distal end of an inserting portion that is inserted into the intraluminal organ, and a distal end portion of the stapling portion is attachably and detachably integrated with an anvil which provides a tissue fixing portion. The anvil is able to staple the tissue by pressing a foot portion of the staple into contact with the staple projected from a stapling portion. Further, a control section is provided on a proximal side of the inserting portion of the tissue stapler.

Recently, there has been proposed an inserting portion to be inserted into the intraluminal organ formed to provide flexibility in consideration of insertability into a deep portion of the intraluminal organ, or promoting insertability by arranging an observing optical system at a distal end thereof (refer to, for example, JP-A-2003-111763, U.S. Pat. No. 5,411,508).

Further, when the intraluminal organs are anastomosed by using the tissue stapler with the promoted insertability of the inserting portion, the inserting portion and the anvil are inserted into the intraluminal organ orally or via the anum. Further, the intraluminal organs are anastomosed at an aimed position in the coelom of the intraluminal organ by confirming a distal end position of the inserting portion and a position of the anvil used in combination with the inserting portion and controlling the movement of at least one of them.

Hence, in addition to anastomosis being assisted by a rigid scope and forceps, recently there has also been proposed a tissue stapler constituted to facilitate operability by opposedly arranging magnets at the anastomosing portion and the anvil to enable their positioning proximate to each other by a magnetic force (refer to, for example, U.S. Pat. No. 5,411,507).

However, although observing optical systems are disclosed in the tissue staplers of JP-A-2003-111763 and U.S. Pat. No. 5,411,508, the apparatus parts, per se are disposed in the intraluminal organ and therefore, in order to execute anastomosis while attracting the organs disposed at positions remote from each other in the coelom, there is need for assistance by a rigid scope and forceps which are transabdominally inserted (introduced). Further, even on the premise of the transabdominal approach, the position of the distal end of the tissue stapler and the position of the anvil disposed in the intraluminal organ need to be confirmed by the rigid scope and grasped to be guided by the grasping forceps and therefore, there is a drawback that handling is awkward.

Further, the tissue stapling system of U.S. Pat. No. 5,411,507 is not useful when the tissues to be anastomosed are not disposed proximate each other, necessitating assistance of a rigid scope and a grasping forceps which are transabdominally inserted. This constitutes a substantial drawback.

The invention has been made in view of the above-described observations and it is an object of the invention to provide a tissue stapler of improved handling operability.

BRIEF SUMMARY OF THE INVENTION

In a staple receiving portion (anvil) of a tissue stapler, the invention features providing a position information transmitting member for transmitting position information.

An embodiment of the tissue stapler includes an inserting portion provided with an endoscope inserting tube path, a stapling portion provided with a staple injecting portion arranged on a distal end side of the inserting portion, and a staple receiving member (anvil) arranged separately from the inserting portion. The staple receiving member is grasped by a treatment tool introduced via the inserting portion in a state where it is juxtaposed to the stapling portion. The staple receiving member is capable of folding (bending) a distal end portion of a staple member penetrating through the tissue, which staple member protrudes from the staple injecting portion of the stapling portion.

According to the above-described constitution, by detecting the position information transmitted from the position information transmitting member at the staple receiving portion, an operator can obtain the position of the staple receiving member in the tissue. Therefore, the operator can grasp the staple receiving portion by operating a treatment tool inserted into the inserting portion based on the position information. Therefore, stapling can be finished conveniently and easily without depending on hunch, and in a swift manner.

BRIEF DESCRIPTION OF THE DRAWINGS

These and other features, aspects and advantages of the apparatus and methods of the present invention will become better understood with regard to the following description, appended claims, and accompanying drawings, where:

DETAILED DESCRIPTION OF THE PREFERRED EMBODIMENTS

An embodiment of the invention will be described below with reference to the accompanying drawings.

Figure 1:
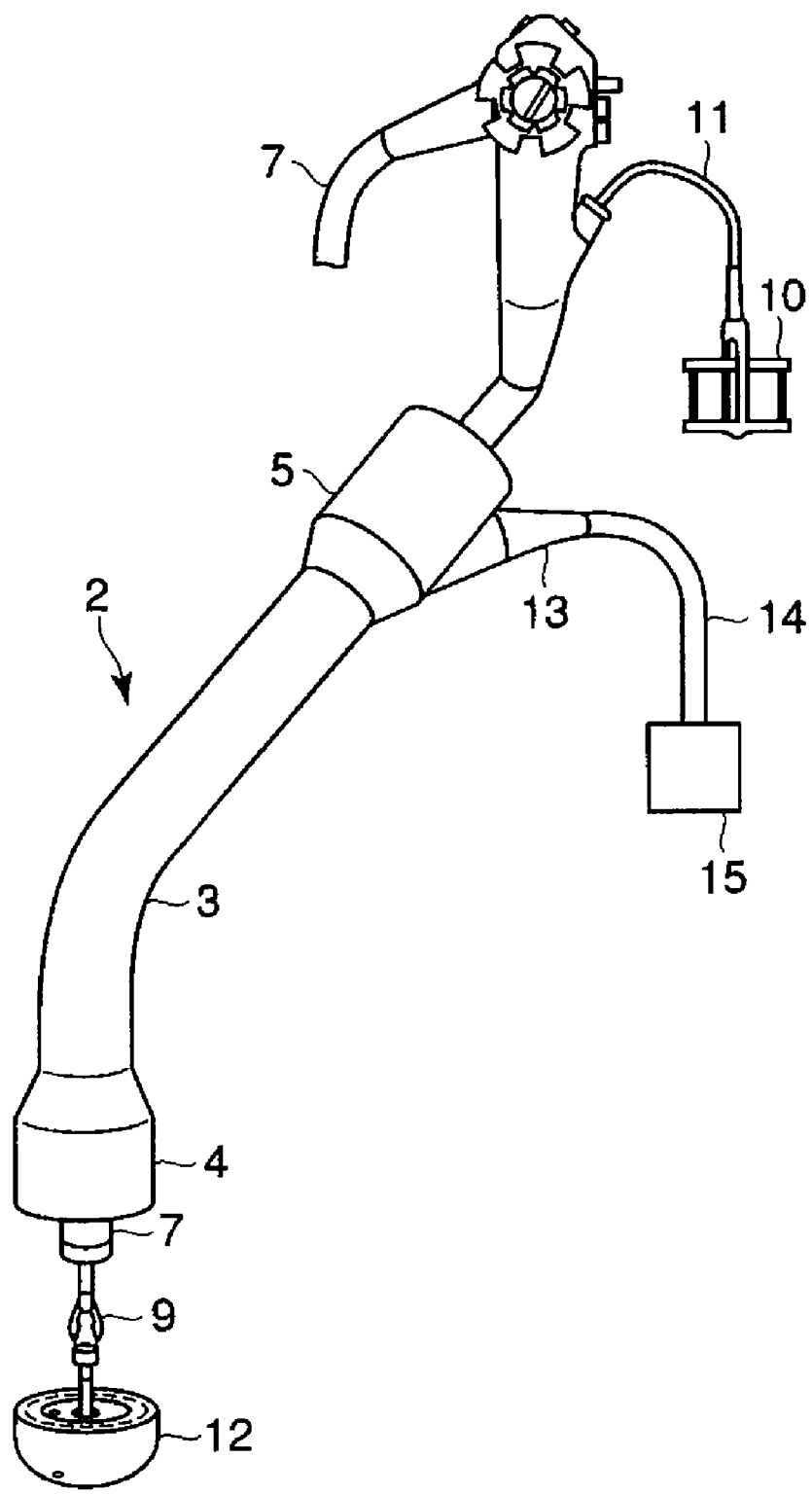
FIG. 1 is a perspective view showing a tissue stapler according to a first embodiment of the invention.

FIG. 1 shows a tissue stapler according to the first embodiment of the invention. The tissue stapler includes an anvil 12 which is a staple receiving member arranged separately from a stapler main body 2.

The stapler main body 2 is provided with a stapling portion 4 on a distal end side of an inserting portion 3 and provided with a proximal side control section 5 on a proximal side of the inserting portion 3. The inserting portion 3 is formed with an endoscope inserting tube path 6 from the stapling portion 4 to the hand-held control section 5 substantially on an axial portion thereof (refer to FIG. 2) and the endoscope inserting tube path 6 is inserted with an endoscope 7. A treatment tool inserting tube path 8 of the endoscope 7 accommodating a treatment tool, for example, an anvil grasping piece 11, and the anvil 12 is detachably grasped by an anvil grasping portion 9 at a distal end of the anvil grasping piece 11. The anvil grasping piece 11 is arranged with a proximal side control section 10 on a proximal side and the proximal side control section 10 is operably located on a proximal side of the inserting portion 3.

Figure 2:
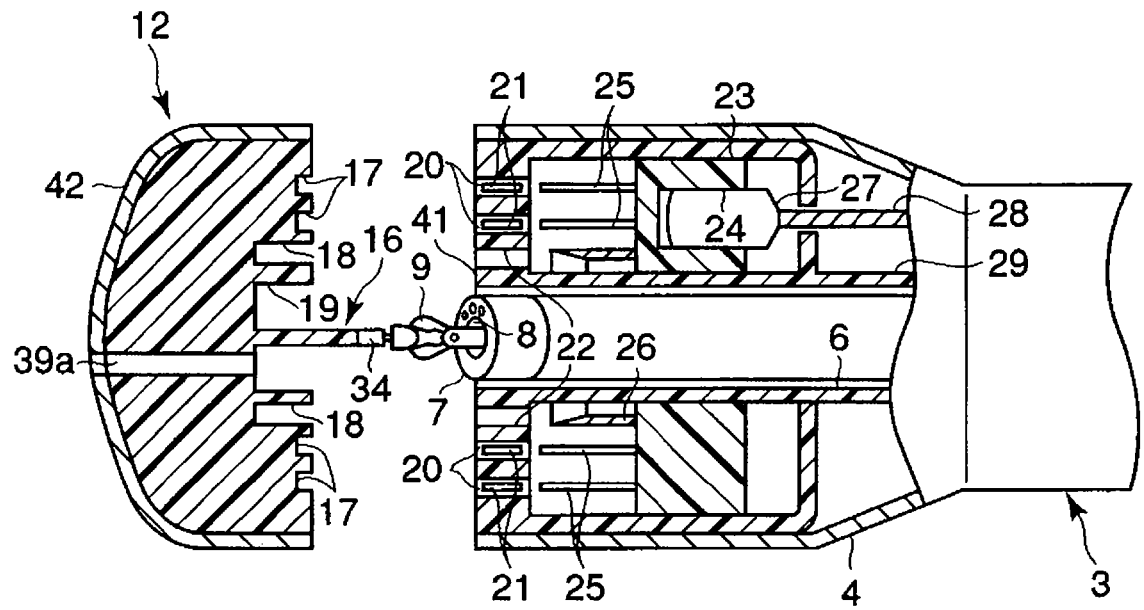
FIG. 2 is a perspective view showing an anvil and a stapling portion of FIG. 1.

The stapling portion 4 is inserted with a staple container 41 that is substantially hollow, and a distal end face of the staple container 41 is provided with a plurality of staple containing holes 20 in double rows, in a ring-like shape (refer to FIG. 2). The staple containing holes 20 are equipped with staples 21, each of which has a substantially horseshoe shape. As shown, the plurality of staple containing holes 20 are arranged alternately on an inner peripheral side and on an outer peripheral side in the ring-like shape aligned in double rows.

Further, the staple container 41 is provided with a cutter member inserting hole 22 in a ring-like shape in parallel with the staple containing hole 20 on an inner peripheral side of the staple containing hole 20. Further, a moving member 23 substantially in a cylindrical shape is movably inserted into the staple container 41 along the axis of the endoscope inserting tube path 6. On end of the proximal side of the moving member 23 is provided with a female screw portion 24, and the screw portion 24 is screwed with a screw member 27. The screw member 27 is connected to a motor unit 15 (refer to FIG. 1), described later, via a cable 28. When the motor unit 15 is driven, a rotational force thereof is transmitted via the cable 28 to adjust the position of the moving member 23 to move the moving member 23 in an axial direction.

The other end of the moving member 23 is provided with a plurality of staple extruding members 25 each substantially in a plate-like shape having a width and a thickness insertable into the staple containing hole 20 at positions corresponding to the respective staple containing holes 20. When the moving member 23 is maximally moved rearward to the proximal side, a distal end of the staple extruding member 25 is disposed at a proximal side end of the staple containing hole 20. Further, in a state of maximally moving forward the moving member 23 to a distal end side, the moving member 23 is urged to move the staple extruding member 25 in the same direction to contact the staple 21 to extrude the staple 21 from a distal end face of the staple containing hole 20.

Further, in an inner side of the staple extruding member 25, there is provided a cutter member 26 having a cylindrical shape entirely surrounding the endoscope inserting tube path 6. A blade tip of the cutter member 26 is contained in the staple containing member 41 of the stapling portion 4 when the moving member 23 is positioned in the most proximal position, and is projected from an distal end face of the stapling portion 4 when the moving member 23 is in the most distal position.

Figure 3:
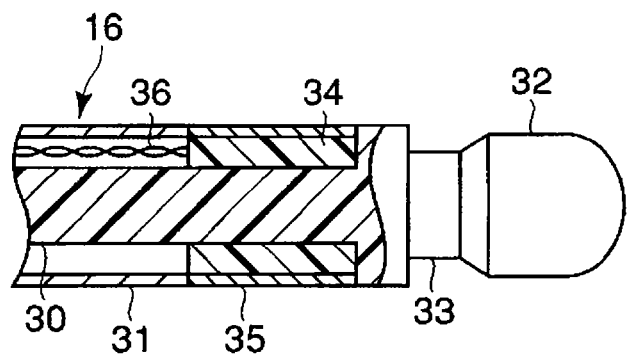
FIG. 3 is a perspective view showing a shaft member of the anvil of FIG. 1.

The anvil 12 includes an anvil main body 42 and a shaft member 16, and the shaft member 16 is formed to have an outer diameter insertable into the endoscope inserting tube path 6. The shaft member 16 is provided with a shaft 30 (refer to FIG. 3) extending from the anvil main body 42, and a distal end side of the shaft 30 is formed with a distal end grasped portion 32 substantially in a spherical shape. Further, a proximal end side (rear end side) of the distal end grasped portion 32 is formed with a fitting groove 33 over an entire periphery of the shaft 16, and the anvil grasping portion 9 detachably grasps at the fitting groove 33.

Further, the shaft 30 is covered with a shaft cover member 31 from a rear portion of the fitting groove 33 to the anvil main body 42. The shaft cover member 31 is provided with a transparent portion 35 at a vicinity of a fitting groove 33, and the shaft 30 inside of the transparent portion 35 is provided with a light emitting member 34 of, for example, an LED or the like constituting a position information transmitting member. The light emitting member 34 is electrically connected to a power source member (not shown) provided in the anvil main body 42 via a cable 36 and emits light by being energized with a power source member (not shown).

The anvil main body 42 is provided with a plurality of recess portions 17 for underfolding (bending) staple feet arranged substantially in a ring-like shape in double rows at positions opposed to the staple containing holes 20 of the stapling portion 4. Further, a cutter member receiving slit 18 substantially in a ring-like shape is provided at a position opposed to the cutter member 26 of the stapling portion 4. Further, the anvil main body 42 is provided with a tissue receiving portion 19 for receiving a tissue to be cut off, surrounding a proximal end of the shaft member 16. The anvil main body 42 is provided with a guide wire inserting hole 39a (through hole) connecting a distal end side thereof and the tissue receiving portion 19 (refer to FIG. 2).

Further, the proximal side control section 5 is extended with a cable tube 14 via an anti-folding member 13, an end portion of the cable tube 14 is electrically connected to the motor unit 15. A motor (not shown) is accommodated in the motor unit 15 and a rotational force of the motor is transmitted to the cable 28. The cable 28 is provided inside of a cable tube path 29 connecting the cable tube 14 and the stapling portion 4, and connected to the screw member 27 for transmitting the rotational force.

Figure 4:
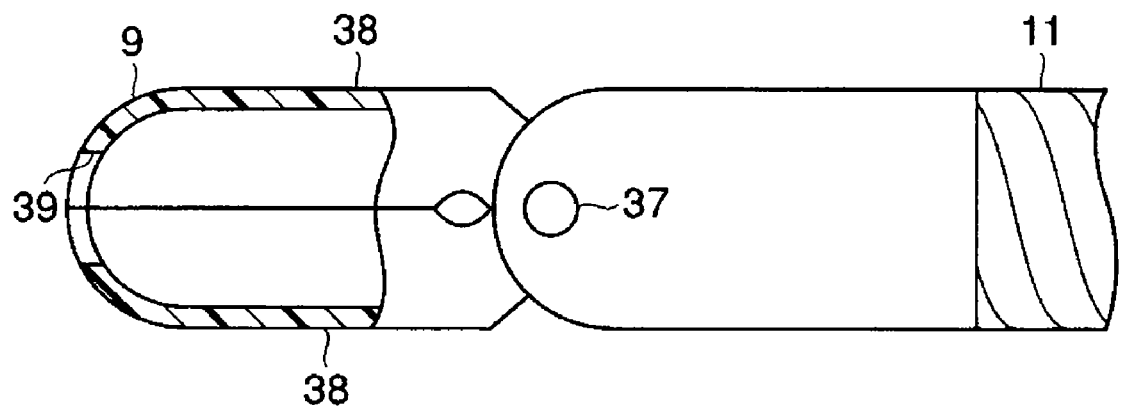
FIG. 4 is a perspective view showing a portion of an anvil grasping piece of FIG. 1.

The anvil grasping piece 11 is provided with the anvil grasping portion 9 to grasp and release the anvil 12 at the distal end thereof. As shown FIG. 4, the anvil grasping portion 9 is provided with a pair of grasping arms 38 substantially in a hollow shape openably and closably pivoted on a shaft 37 provided at a distal end of the inserting portion 3, and distal end portions of the grasping arms 38 are provided with a grasping groove 39 which forms an opening in a closed state of the grasping arms 38. When the grasping arms 38 are closed, the grasping groove 39 is fitted with the fitting groove 33 of the anvil 12. The pair of grasping arms 38 of the anvil grasping portion 9 are connected to the proximal side control section 10 arranged on the proximal side of the inserting portion 3 by a link mechanism (not shown) and an operating wire (not shown). The grasping arms 38 are operated to open and close via the operating wire and the link mechanism by an open-close operation of the proximal side control section 10.

Figure 5:
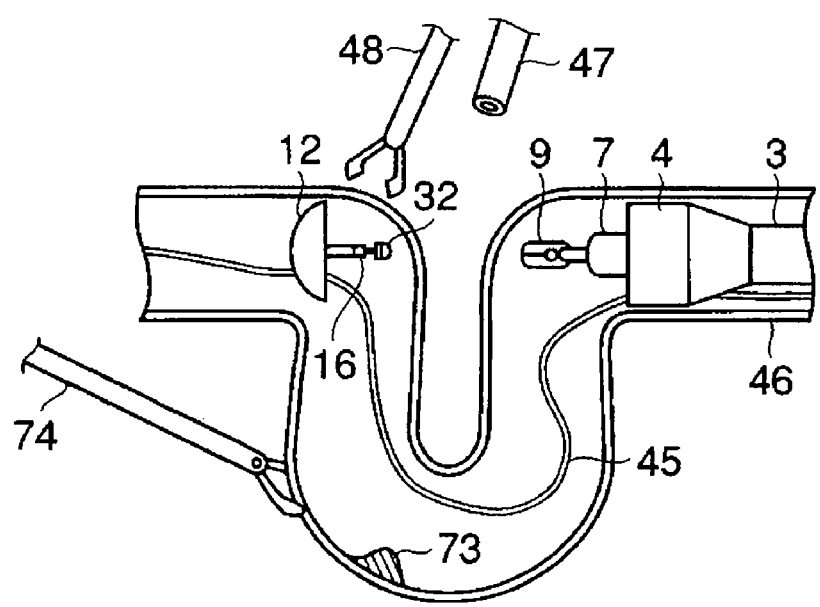
FIG. 5 is a view showing a state of inserting the anvil and the stapling portion of FIG. 1 into the tissue.

In the above-described configuration, when a tissue, for example a large intestine, is partially cut off to be stapled, an operator initially inserts a guide wire 45 to a deep portion of the large intestine 46 per anum as shown in FIG. 5. Further, the operator inserts the anvil 12 passed through the guide wire inserting hole 39a from the anus side end of the guide wire 45 to a position beyond a morbid portion 73 following the guide of the guide wire 45. Next, the operator inserts the inserting portion of the stapler main body 2 with the endoscope 7 inserted in the endoscope inserting tube path, into the large intestine 46 per anum. The endoscope, as a position detecting device, reaches near the morbid portion 73 and stops at the anum side thereof in the intestine 46.

At this point, the operator confirms the positions of the anvil 12 and the inserting portion 3 of the stapler main body 2 by a rigid scope 47 inserted transabdominally. At this time, since the light emitting member 34 in the shaft 30 and the endoscope 7 inserted into the inserting portion 3 are emitting light, the position of the anvil 12 is determined by observing the light through enteron wall of the large intestine 46. Thus the light of the anvil provides position information.

Further, while the operator is grasping a vicinity of the morbid portion 73 of the large intestine 46 with a grasping forceps 74 which is a guiding member inserted into the coelom transabdominally and moving the grasping portion to one side, the operator drags the anvil 12 to a vicinity of the stapling portion 4 of the inserting portion 3 by the other grasping forceps 48.

Figure 6:
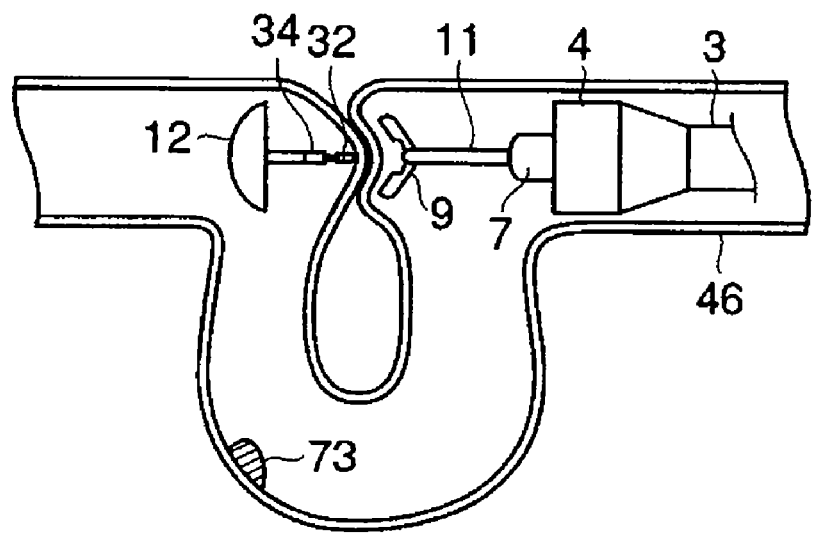
FIG. 6 is a view showing a state of grasping the anvil by the anvil grasping piece via the tissue follows the state of FIG. 5.
Figure 7:
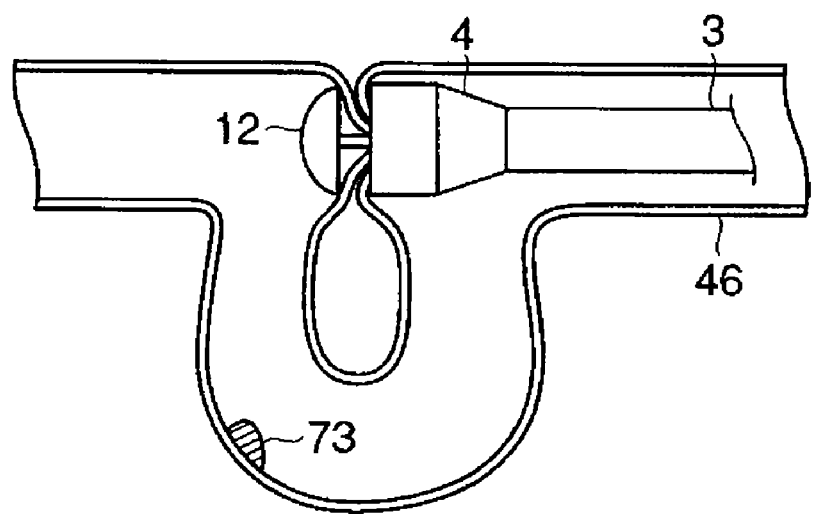
FIG. 7 is a view showing a state of grasping the anvil by the anvil grasping piece via the tissue follows the state of FIG. 6.

Thus, a side face and another side face of the large intestine 46 near each other as the intestine forms a loop, and the anvil 12 and the stapling portion 4 of the inserting portion 3 come closer to each other. The operator detects light emitted from the light emitting member 34 of the anvil 12 with the endoscope 7 by reducing an emitted light amount of the rigid scope 47 in a state of making the anvil 12 and the stapling portion 4 proximate to each other. When the shaft 30 is grasped by the anvil grasping piece 11 with the enteron wall using the light as a guide, the distal end grasped portion 32 of the anvil 12 is contained in the hollow portion of the grasping arms 38 and the grasping groove 39 of the grasping arms 38 are fitted together with the fitting groove 33. Thereby, the distal end grasped portion 32 is firmly grasped are held by the anvil grasping piece 11 (refer to FIG. 6 and FIG. 7).

Next, the operator drags the endoscope 7 and the anvil grasping piece 11 into the endoscope inserting tube path 6, while grasping the anvil 12 along with the large intestine 46. This interposes the large intestine wall of two layers between the anvil 12 and the stapling portion 4 of the inserting portion 3. At this point, the cable 28 is rotated by driving the motor unit 15. Then, the rotational force of the cable 28 is transmitted to the screw member 27, the screw member 27 is driven to rotate and the moving member 23 is moved linearly in the direction of the distal end.

As a result, the moving member 23 pushes the staple extruding member 25 in the distal direction, which extrudes the staple 21 from the staple containing hole 20.

Then, the distal end portion of the staple 21 pierces through the intestine wall of two layers and press contacts with the recess portion 17 of the anvil main body 42. Thereby, the foot of the staple is underfolded to an inner side along the shape of the recess portion 17 to staple the large intestine wall. Further, the cutter member 26 projects from the stapling portion 4 responsive to the moving member 23 to cut the large intestine wall to form the anastomosed opening portion 49. At this point, the blade tip is received in the cutter member receiving slit 18. The tissue cut off by the cutter member 26 is captured in the tissue receiving portion 19.

Figure 8:
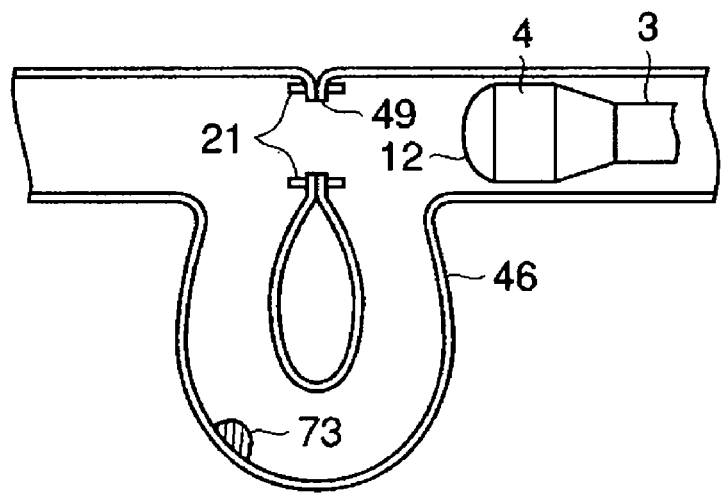
FIG. 8 is a view showing a state of subjecting the tissue to the stapling and anastomosing treatment follows the state of FIG. 7.

At a stage of finishing to staple and cut off the large intestine wall in this way, the anvil grasping piece 11 is temporarily moved forward to form a gap between the anvil 12 and the stapling portion 4, then the large intestine 46 stapled by the staple 21 is released, thereafter, the inserting portion is drawn out (refer to FIG. 8).

Figure 9:
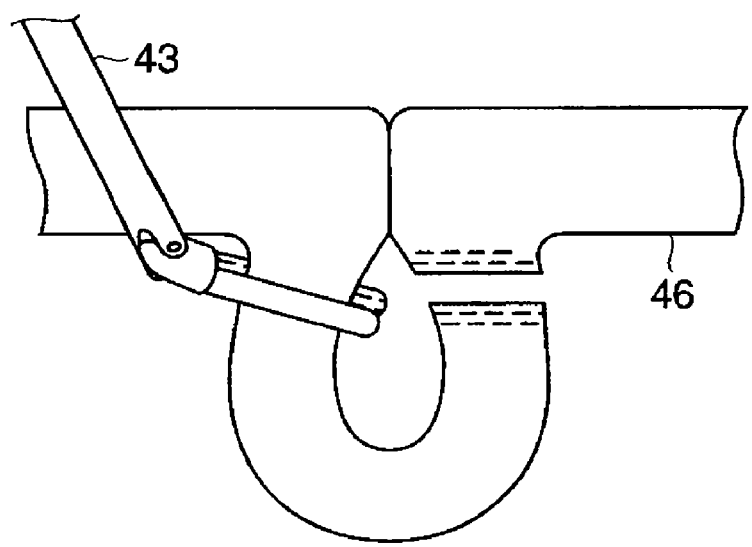
FIG. 9 is a view showing a state of separating the stapled portion from a state of finishing to staple and the tissue anastomose of FIG. 8.

Thus, the large intestine 46 substantially formed in the loop shape has, the side faces of the enteron anastomosed, incorporating the morbid portion 73 in the loop portion. The operator cuts off and staples each root portion of the loop by a tissue staple remover 43 inserted into the enteron transabdominally (refer to FIG. 9).

Although an explanation has been given of a procedure of cutting off a large intestine portion, the operation is not limited thereto but can similarly be carried out to staple other tissue types. That is, the operator inserts the anvil 12 constituting the staple receiving member provided with the light emitting member 34 constituting a position information transmitting member into the first tissue and inserts the inserting portion 3 into the second tissue. According to the described embodiment, the inserting portion 3 includes the stapling portion 4, integrated with the anvil 12, provided with the plurality of staple injecting portions substantially in the ring-like shape and the endoscope 7 with the anvil grasping piece 11 is inserted into the inserting portion 3.

Next, the operator determines the position of the anvil 12, by detecting the position information from the light emitting member 34 of the anvil 12, using at least one of, for example, the endoscope 7 inserted into the inserting portion 3 or the anvil grasping piece 11 mounted to the endoscope 7, or the rigid scope 47 inserted transabdominally. Further, the anvil 12 is grasped by the anvil grasping piece 11 via the first and the second tissue, being guided by the anvil grasping piece 11 or the grasping piece inserted transabdominally, for example, by the grasping forceps 48 serving as a guiding member. Thereafter, the operator performs the stapling treatment by the stapling portion 4 of the inserting portion 3 and the anvil 12.

Further, although in the above-described stapling treatment procedure, an explanation has been given of a case in which the transabdominally inserted rigid scope 47 and the grasping forceps 48 are used as the position information detecting member for detecting the position information from the anvil 12 and as the guiding member for guiding the anvil 12 based on the detected position information, the procedure is not limited thereto. For example, the guiding members may be constituted by using the endoscope 7 mounted to the inserting portion 3 and the anvil grasping piece 11.

As described above, the tissue stapler is constituted such that the anvil 12 is arranged with the light emitting member 34 and the anvil 12 is grasped to be attached to the stapling portion 4 by the anvil grasping piece 11 of the endoscope 7 inserted through the inserting portion 3 by specifying the position of the anvil 12 based on the position information from the light emitting member 34.

Thus, high accuracy guiding can be obtained by detecting the position information of the anvil 12 by the rigid scope 47 inserted transabdominally and using the grasping forceps 48, similarly inserted, and the anvil can firmly be grasped to be fixed swiftly and easily.

For example, under the assistance of the grasping forceps 48, by having the anvil 12 located in the tissue such as a large intestine lumen approach to the stapling portion 4 of the inserting portion 3, the operator can identify the anvil 12 transabdominally with the endoscope and easily execute an anastomosis operation.

Further, the lumen of the large intestine or the like can be cut off and anastomosed without cutting the enteron wall and highly reliable and highly accurate cutting and anastomosing treatment can be carried out.

Further, the structure of an anvil grasping portion of the anvil grasping piece 11 mounted to the endoscope 7 is not limited to a constitution described above. Rather, the structure is similarly effective even when constituted as shown by FIGS. 10, 11, 12, 13 and 14. In FIG. 10 through FIG. 14, the same portions as those of FIG. 1 through FIG. 9 are annotated with the same reference characters and the explanation thereof is omitted.

Figure 10:
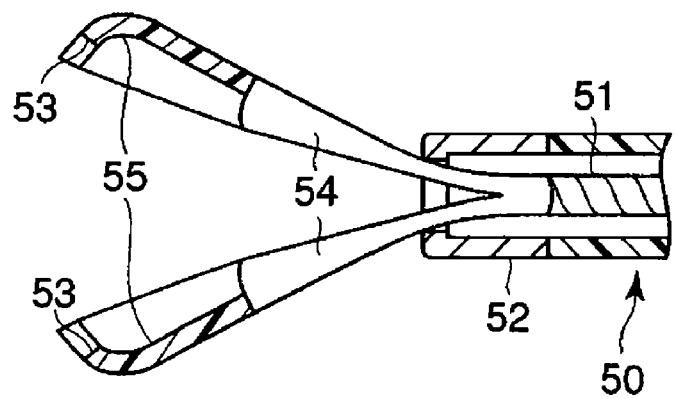
FIG. 10 is a view showing another example of an anvil grasping portion applied to the first embodiment.

According to the structure of the anvil grasping portion of FIG. 10, an anvil grasping portion 50 comprises an operating wire 51 connected to the proximal side control section 10 and inserted into a distal end portion of a sheath 52, and a pair of grasping arms 54 are arranged openably and closably at a distal end portion of the operating wire 51. The pair of grasping arms 54 are arranged expandably in a state of being projected from the distal end portion of the sheath 52, and distal end sides thereof are provided with grasping grooves 53 having an opening diameter portion capable of being fitted to the fitting groove 33 of the shaft 30 of the anvil 12 and hollow portions 55 for accommodating the distal end grasped portion 32 of the anvil 12.

Figure 11:
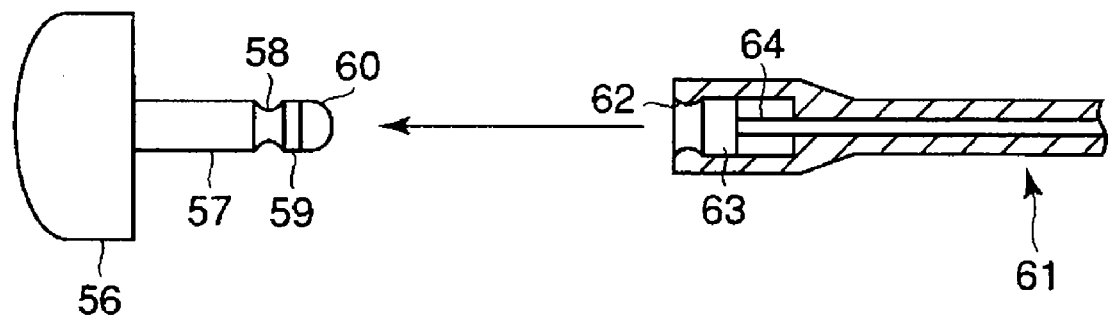
FIG. 11 is a view showing another example of the anvil grasping portion applied to the first embodiment.
Figure 12:
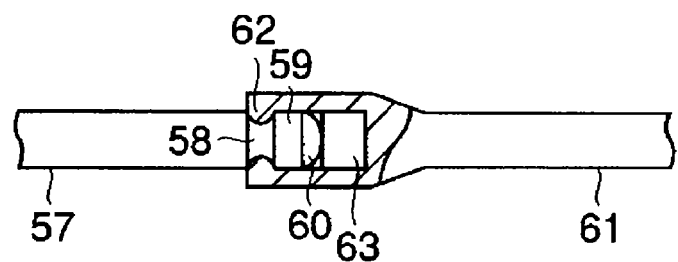
FIG. 12 is a view showing a state of grasping to fix the tissue of FIG. 11.

Further, according to the structure of the anvil grasping portion of FIG. 11 and FIG. 12, a distal end side of a shaft member 57 of an anvil 56 is provided with a fitting groove 58 and a distal grasping portion 59 in this order, and a distal end side of the distal end grasping portion 59 is provided with a magnet member 60 serving also as a position information transmitting member. Further, a distal end portion of an anvil grasping portion 61 used in combination with the anvil 56 is provided with a recess portion 62 in correspondence with the fitting groove 58 of the shaft member 57. Further, a magnet member 63 also serving as a position information transmitting member in cooperation with the magnet member 60 is accommodated in the recess portion 62 in an axially movable direction. The magnet member 63 is connected with an operating wire 64 that can be moved forwardly and backwardly with the operation of the proximal side control section 10.

In the above-described constitution, the anvil 56 is inserted into the lumen of, for example, the small intestine or the like, the anvil grasping piece 61 is placed proximate to the anvil 56, the operating wire 64 is extruded by operating the proximal side control section 10, and the magnet member 63 is projected from the anvil grasping portion 61. Then, the magnet member 63 and the magnet member 60 of the anvil 56 attract each other magnetically, to become positioned proximate to each other. At this point, by drawing the operating wire 64 by operating the proximal side control section 10 again, the shaft member 57 is drawn into an inner portion of the anvil grasping portion 61, and the projected portion 62 is fitted to the fitting groove 58 to become fixedly grasped thereby (refer to FIG. 12). The magnetic force between the magnet member 60 and the magnet member 63 increases the grasping strength and fixing of the anvil.

Figure 13:
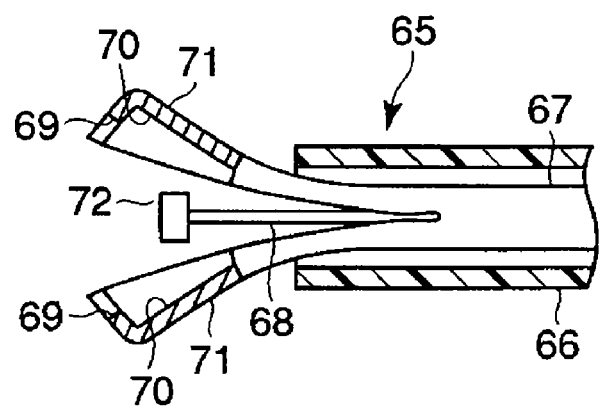
FIG. 13 is a view showing another example of the anvil grasping portion applied to the first embodiment.
Figure 14:
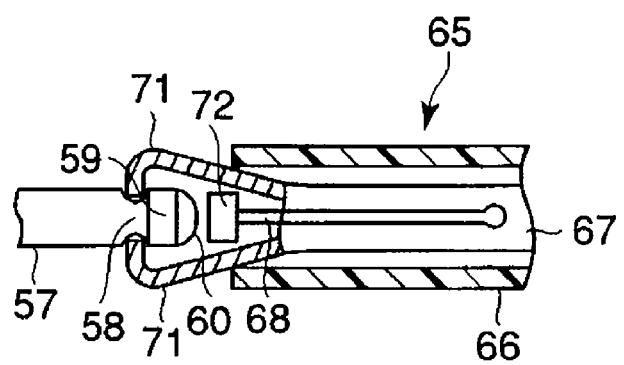
FIG. 14 is a view showing a grasping and fixing state of FIG. 13.

According to a structure of an anvil grasping portion of FIG. 13 and FIG. 14, the anvil grasping portion 65 comprises an operating wire 68 connected to the proximal side operating portion 10, inserted into an operating tube 67. The operating tube 67 is movably inserted into an inserting sheath 66, to move axially therein. Further, a distal end of the operating tube 67 is provided with a pair of grasping arms 71 that are capable of being opened and closed, when the arms project from the inserting sheath 66. Distal ends of the grasping arms 71 are provided with grasping grooves 69 having a diameter of an opening fitted to the fitting groove 58 of the shaft member 57 (refer to FIG. 11), and hollow portions 70 for accommodating the distal end grasping portion 59.

Further, a magnet 72 is provided at a distal end of the operating wire 68, in correspondence with the magnet 60 of the shaft member 57 of the anvil 56, in a manner that enables it to be extracted and retracted from and to the distal end of the inserting sheath 66 by being moved in the axial direction inside of the inserting sheath 66 along with the operating tube 7.

In the above-described embodiment, the operator first places the anvil holding portion 65 proximate to the anvil 56 inserted into the lumen, for example, the small intestine or the like extruding the operating tube 67 and the operating wire 68 by operating the proximal side control section 10. Then, the magnet 60 of the anvil 56 and the magnet 72 of the operating wire attract and approach each other is magnetically.

The operating wire 68 is then drawn into the operating tube 67, and the operating tube 67 is drawn into the inserting sheath 66. Then, the grasping arms 71 are closed through the above drawing operations, and the grasping grooves 69 become fitted to the fitting groove 58 of the shaft member 57 of the anvil 56 and the anvil 56 is fixedly grasped by the anvil grasping portion 65.

Further, although the embodiment has been explained for the case where the position information transmitting member utilizes the light emitting member 34 and the magnetic force of the magnet members 60, 63, the utility of the position information transmitting member is not limited to this precise embodiment. For example, the position information transmitting member may be formed to transmit an electromagnetic wave such as visible light or the like as position information. The position information transmitting member and a position detecting member for detecting the position information may be a device that converts electric energy into visible light or the like, for example, a semiconductor LED or organic EL, a semiconductor laser, a device that emits light by a chemical reaction using luminol, or a fluorescent substance emitting fluorescence light induced by light emitted from the endoscope.

Luminescence of green color or blue color is particularly effective, since the luminescence of these colors is easy to detect in the coelom.

Further, the emitted light energy is not limited to visible light, but may be, for example, radio wave, X-ray, gamma ray or the like having extremely shorter wavelengths, or infrared radiation having a longer wavelength. Further, the transmitted energy may be radiated as wave energy or as supersonic, acoustic energy, or the like. Detecting the position information can be effected, other than through detection of light by CCD or the like provided at a distal end of the endoscope. Thus, the method of detecting radio wave by an antenna, detecting a magnetic field by a Hall element or the like, detecting radioactive ray by a scintillator, detecting supersonic wave by a transducer or the like can be utilized.

Although the first embodiment has been explained for the case in which the anvil grasping piece 11 as a treatment tool is inserted into the inserting portion 3 via the endoscope 7, the first embodiment is not limited thereto. For example, the anvil grasping piece 11 can be directly inserted into the endoscope inserting tube path 6 of the inserting portion 3.

Figure 15:
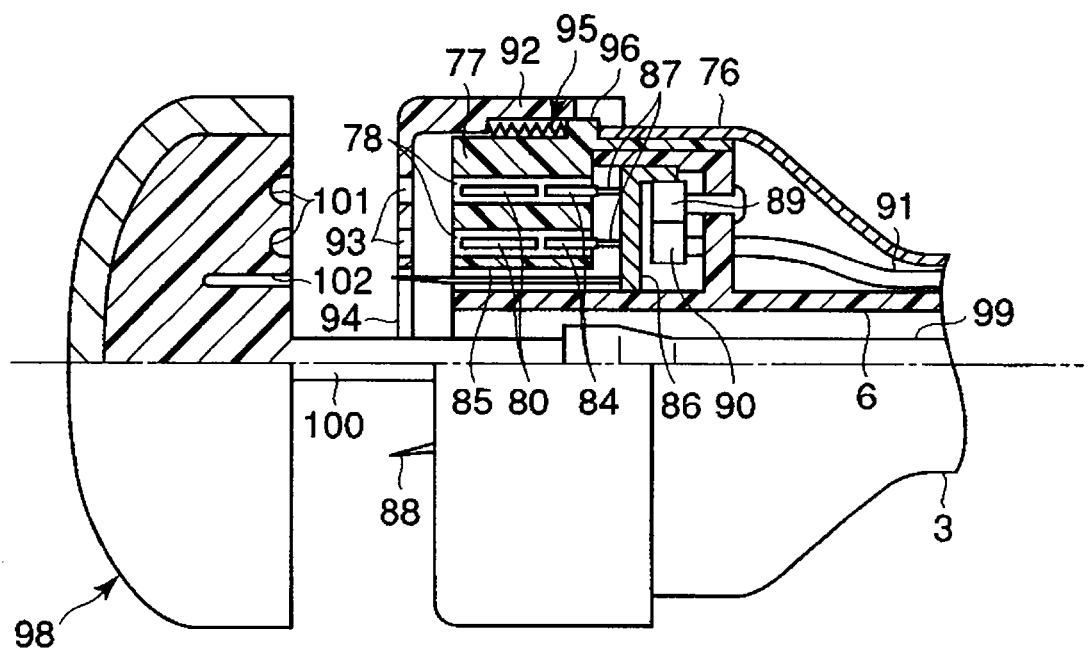
FIG. 15 is a perspective view showing a portion of a tissue stapler according to a second embodiment of the invention.
Figure 16:
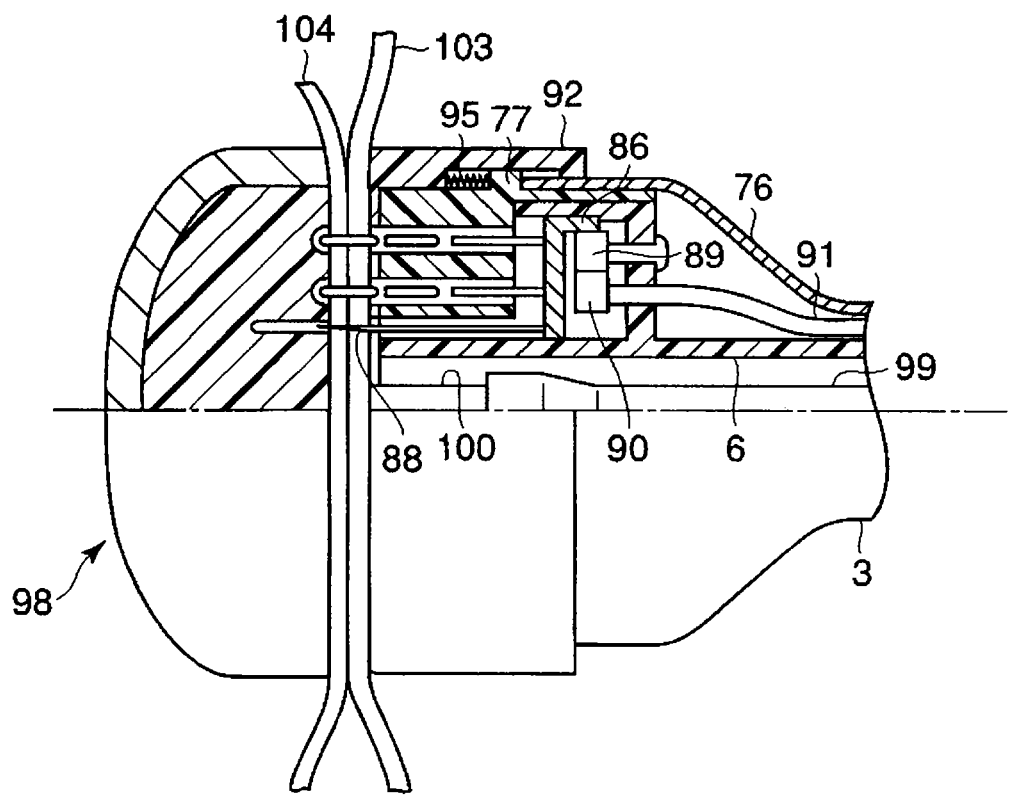
FIG. 16 is a view showing a state of stapling the tissue according to FIG. 15.

FIG. 15 and FIG. 16 show a main portion of a tissue stapler according to a second embodiment of the invention. FIG. 15 shows a grasping state and FIG. 16 shows a stapling state. FIG. 15 and FIG. 16 also show previously described portions identified by the same reference numerals.

Figure 17:
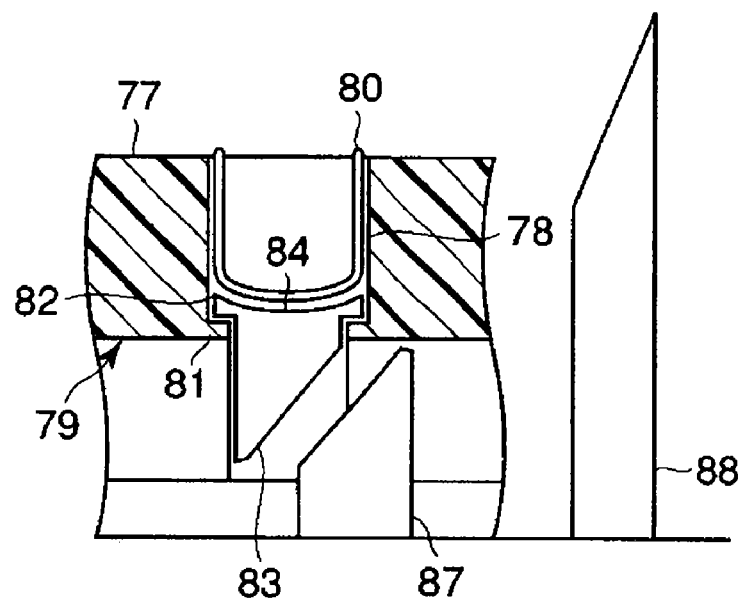
FIG. 17 is a view showing a state before stapling tissue by a stapling portion of FIG. 15.
Figure 18:
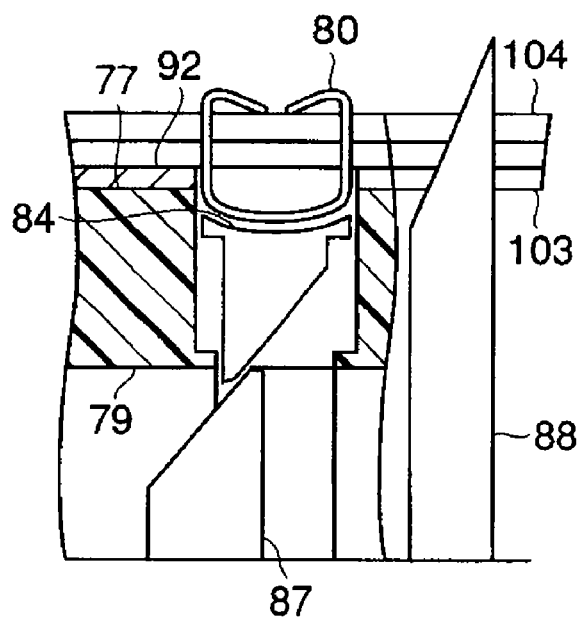
FIG. 18 is a view showing a state of stapling the tissue of FIG. 17.

That is, a stapling portion 76 is provided at the distal end portion of the inserting portion 3 and is inserted with a staple container 77 substantially in a ring-like shape. A distal end face of the staple container 77 is provided with a plurality of staple containing holes 78 arranged in double rows in a ring-like shape. The staple containing holes 78 are provided such that positions of the holes are alternate to each other on an outer side and an inner side. A proximal side end of the staple container 78 is provided with a staple slide slit 79 in a ring-like shape in the form of following the staple containing holes 78 as shown by FIG. 17 and FIG. 18.

The staple containing holes 78 contain the staples 80 bend in a horseshoe-like shape. The proximal sides of the staples 80 are oppositely arranged with staple extruding members 84. The staple extruding member 84 is provided with a projected portion 82 brought into contact with the staple 80 and brought into contact with a projected portion 81 provided on a proximal side of the staple containing hole 78. The staple extruding member 84 is also provided with a projected portion 83 projecting into the staple side slit 79 on a proximal side of the projected portion 81. The projected portion 83 of the staple extruding member 84 is provided with an inclined face.

Further, the staple containing member 77 is provided with a cutter member inserting hole 85 substantially in a ring-like shape on an inner peripheral side of the staple containing hole 78. Further, a proximal side of the staple container 77 is arranged with a rotating member 86 substantially cylindrically shaped and having a plane at a distal end side thereof, the rotating member can rotate around the axis of the endoscope inserting tube path 6. A distal end face of the rotating member 86 is provided with a staple slider 87 substantially in a plate-like shape. A distal end portion of the staple slider 87 is provided with an inclined face, and the inclined face is designed to contact with the inclined face of the projected portion 83 (refer to FIG. 17). Further, an inner peripheral side of the staple slider 87 is provided with a cutter member 88 substantially in a shape of a thin plate. A blade tip of the cutter member 88 is projected from the staple containing member 77 to a distal end side, being inserted through the cutter member inserting hole 85.

A proximal side of the rotating member 86 is substantially cylindrical in shape, and an inner wall side thereof is provided with a gear (not shown). A gear member 89 is meshed with the gear (not shown). A drive gear 90 is brought in mesh with the gear member 89. The drive gear is connected to the motor unit 15 via a cable 91, and is driven to rotate by the driving force transmitted via the cable 91 from the motor unit 15.

A distal end side of the staple container 77 is covered with a cover member 92. The cover member 92 is provided with a plurality of staple inserting holes 93 in double rows substantially in a ring-like shape at positions opposed to the staple containing holes 78. An inner peripheral portion of the staple inserting holes 93 is provided with a center hole 94, corresponding to the cutter inserting hole 85. Further, in an interval between the cover member 92 and the staple container 77, a spring member 95 is engagingly provided to push the cover member 92 to the distal direction relative to the staple container 77. The cover member 92 is not detached from the staple container 77 because a projection provided on an inner wall of the proximal side of the cover member 92 abuts a projected member 96 of the staple container 77.

Further, an anvil 98 projects with a shaft member 100 substantially at a central portion thereof, which shaft member is to be fixedly grasped by an anvil grasping piece 99 inserted through the endoscope inserting tube path 6. Further, a surrounding portion of the shaft member 100 is provided with a plurality of recess portions 101 in double rows substantially in a ring-like shape at positions opposed to the staple containing holes 78 and the staple inserting holes 93. Further, a cutter receiving slit 102 is provided at a position opposed to the cutter inserting hole 85.

Further, although not illustrated in FIG. 15 and FIG. 16, the anvil 98 is provided with, for example, the light emitting member 34 as the position information transmitting member, similar to the shaft member 100, position information being emitted via the light emitting member 34.

In the above-described embodiment, when a lumen wall such as the stomach wall 103 and the small intestine wall 104 are to be stapled, the operator first positions the stomach wall 103 and the small intestine wall 104 between the stapling portion 76 and the anvil 98. This is done by grasping the shaft member 100 of the anvil 98 by operating the anvil grasping piece 99 integrated to the endoscope 7 inserted through the inserting portion 3 based on position information from the anvil 98. In this state, when the operator drags the anvil grasping piece 99 into the endoscope inserting tube path 6, the cover member 92 is pressed to the proximal side against the biasing force of the spring member 95. Thereby, the blade tip of the cutter member 88 projects from a distal end face of the cover member 92 through the cutter member inserting hole 85 and the center hole 94 and is received in the cutter receiving slit 102 while piercing through the stomach wall 103 and the small intestine wall 104. In this way, the stapling portion 76, the stomach wall 103, the small intestine wall 104 and the anvil 98 come into close contact with each other (refer to FIG. 16, FIG. 18).

At this stage, the operator drives the motor unit 15 of the inserting portion 3, whereby the drive force of the motor unit 15 rotates the cable 91, to rotate member 86 via the drive gear 90 and the gear 89. The rotating member 86 moves the staple slider 87 in sliding contact with the inclined face of the projected portion 83 in the staple slide slit 79 and causes the staple extruding member 84 and the staple 80 to extrude to the distal end side. Then, the foot portion of the staple 80 pierces the stomach wall 103 and the small intestine wall 104 by being inserted through the staple inserting hole 93, and contacts the recess portion 101 of the anvil 98 disposed at a position opposed thereto. The foot portion is bend to an inner side along the recess portion 101 to staple the stomach wall 103 and the small intestine wall 104 together.

At the same time, the staple slider 87 rotates the cutter member 88 along the cutter inserting hole 85 in accordance with rotation of the rotating member 86 to cut off the stomach wall 103 and the small intestine wall 104 with the blade tip portion piercing through the stomach wall 103 and the small intestine wall 104.

According to the second embodiment, by enabling cutting the tissue in the ring-like shape by using the cutter member 88 substantially in a plate-like shape, the force exerted on constituent parts of the staple extruding member 84, the cutter member 88 and the like and the tissue can be reduced. Therefore, injury to tissue such as debridement or the like can be prevented. Further, slender diameter formation of the driving cable 91 and simplification of the constitution can be achieved with a reduction in the drive force.

Figure 19:
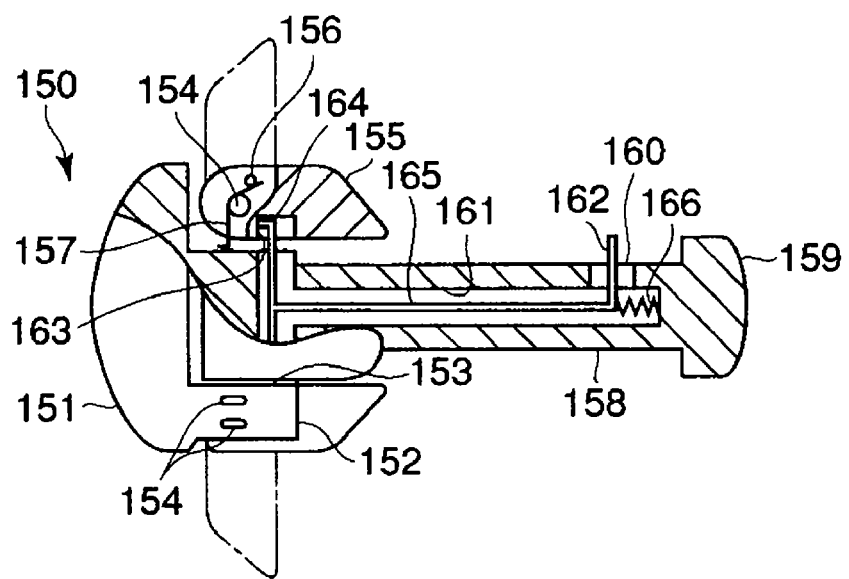
FIG. 19 is a view sectioning to show a portion of an anvil of a tissue stapler according to a third embodiment of the invention.

FIG. 19 shows a main portion of a tissue stapler according to a third embodiment of the invention, portions previously described bearing the same reference notations and providing equivalent function.

Figure 20:
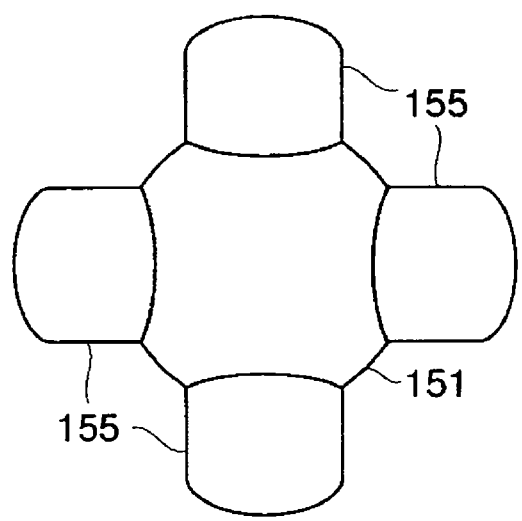
FIG. 20 is a view showing a state of expanding an anvil arm of the anvil of FIG. 19.

Thus, an anvil 150 has an anvil distal end portion 151 with a spherical face at one end face of an anvil main body 152 (refer to FIG. 19 and FIG. 20), a proximal side of the anvil main body 152 constituting the other face which projects to face a shaft member 158 having a distal end grasped portion 159 substantially at a center portion thereof. Further, a surrounding portion of the anvil main body 152 is provided with anvil arm accommodating portions 153 in a recess shape at a plurality of portions thereof, for example, at four portions thereof substantially in a cross-like shape. The anvil arm accommodating portions 153 are provided with anvil arms 155 constituting staple receivers able to be folded and expanded via pivoting shafts 154 thereof.

The anvil arms 155 are respectively attachedly engaged with wound spring members 157 between the pivoting shafts 154 and projected portions 156 to exert biasing forces in the expanding directions, and when the anvil arms 155 expand around the pivoting shafts by the biasing forces of the wound spring members 157, the anvil arms 155 project from the anvil main body 152 in the peripheral directions. Further, the anvil arms 155 can be rotated reversely against biasing forces of the wound spring members 157 to be folded and accommodated in the anvil arm accommodating portions 153. Thereby, the outer shape of the anvil 150 becomes substantially similar to an outer shape dimension of the anvil main body 152 to be brought into a so-called small diameter formation.

The anvil arms 155 are respectively provided with locking portions 163 in a recess shape on proximal sides thereof, and projected portions 164 formed radially at one end of an operating wire 165 are selectively locked by the respective locking portions 163. A middle portion of the operating wire 165 is loosely inserted into a wire inserting tube path 161 provided at the shaft member 158 movably in the axial direction. A base end portion of the operating wire 165 is provided with an operating portion 162 and the operating portion 162 is projected to a slit 160 provided at a shaft member 158 to be able to be operated to move axially. The operating wire 165 is subjected to a biasing force in a direction of the anvil main body via a spring member 166. When the operating portion 162 is grasped by an anvil grasping piece 170, the operating portion 162 is moved in the direction of the proximal side against a biasing force of the spring member 166 and the plurality of projected portions 164 are respectively detached from the locking portions 163 of the anvil arms 155.

Further, although not illustrated in the drawing, the anvil 150 is provided with, for example, the aforementioned light emitting member 34 as the position information transmitting means similar to the first embodiment, in correspondence with, for example, the shaft member 158 so that position information is transmitted via the light emitting member 34.

A distal end side of an inserting portion 169 constituting the tissue stapler is provided with a stapling portion 172. The stapling portion 172 is provided with, for example, wide portions 172*a* at four portions thereof substantially in a cross-like shape in correspondence with the anvil arms 155 of the anvil 150. The wide portion 172*a* has a shape corresponding to the state of the expanding the anvil arm 155, and is provided with, for example, the staple containing hole 20 and the cutter member inserting hole 22 similar to the first embodiment. Further, the stapling portion 172 is provided with an endoscope inserting tube path 178 similarly inserted with the endoscope 7 inserted with the anvil grasping piece 170.

Figure 21:
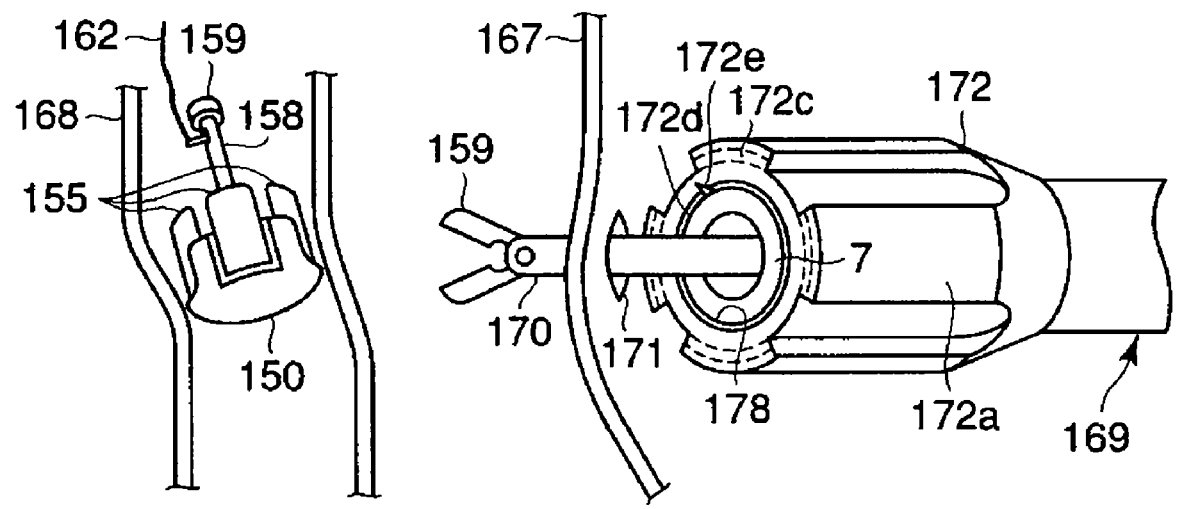
FIG. 21 is a view showing an initial state of grasping to fix the tissue by an anvil grasping piece on a side of a stapling portion of the anvil of FIG. 19.
Figure 22:
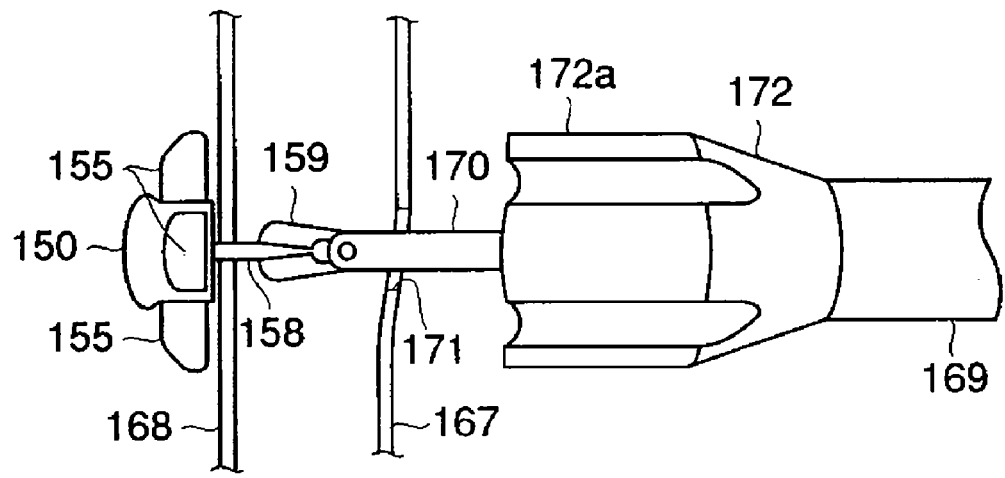
FIG. 22 is a view showing a state of grasping the anvil of FIG. 21 by the anvil grasping piece.

In the above-described embodiment, the operator inserts the anvil 150, for example, orally into the small intestine 168 with the anvil arms 155 folded around the pivoting shafts to be contained in the anvil arm accommodating portions 153. On the other hand, the operator inserts the inserting portion 169 into the stomach 167 constituting the other lumen, for example, orally, by cutting a portion of the stomach 167 to approach the coelom from an opening portion 171 thereof (refer to FIG. 21). At this point, the operator confirms the position of the anvil 150 based on the position information from the anvil 150 in the small intestine 168, and cuts a corresponding portion of the small intestine 168. The operator grasps the anvil shaft member 158 by the anvil grasping piece 170 along with the distal end grasping portion 159 and an operating portion 162 of the operating wire 165 (refer to FIG. 22).

Next, the operator draws the anvil grasping piece 170 into the inserting portion. Then, the operating portion 162 of the operating wire 165 is moved to the proximal side by the anvil grasping piece 170 against the biasing force of the spring member 166 and the projected portions 164 are detached from the locking portions 163 of the anvil arms 155. Thereby, the anvil arms 155 pivot and expand outwardly around the pivoting shafts due to the biasing forces of the wound spring members 157, becoming detached from the anvil arm accommodating portions 153. At the same time, when the anvil grasping piece 170 is drawn into the inserting portion 169, the anvil arms 155 of the anvil 150 contact the wide portions 172a of the stapling portion 172, the stomach wall and the small intestine wall being interposed therebetween.

Figure 23:
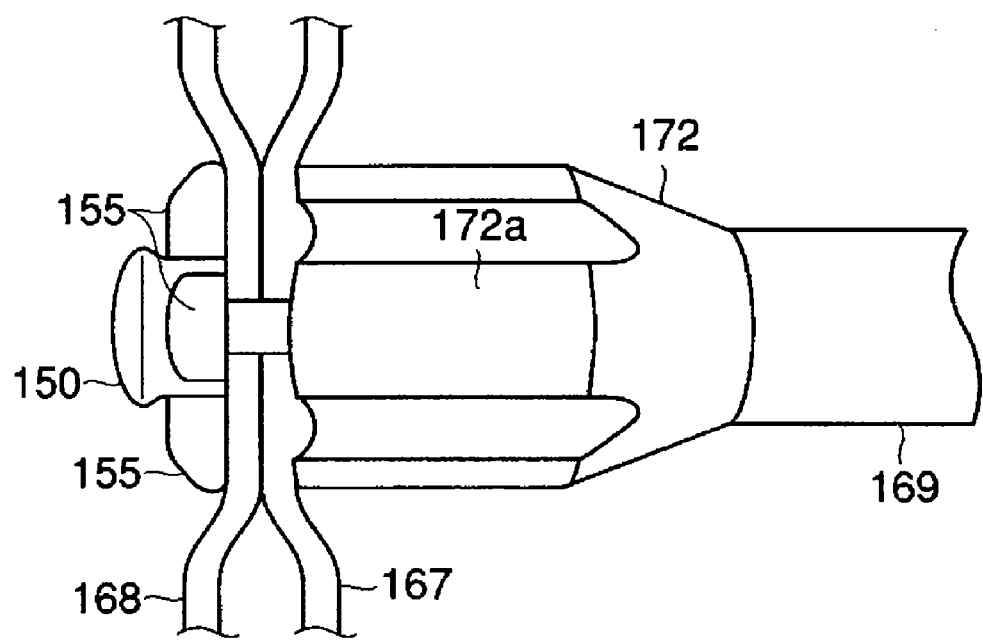
FIG. 23 is a view showing a state of grasping to fix the anvil of FIG. 21 by the anvil grasping piece.
Figure 24:
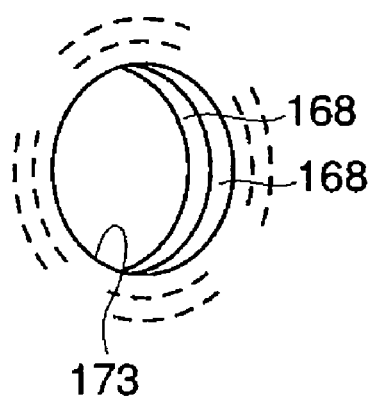
FIG. 24 is a view showing a state of subjecting the tissue to the stapling and anastomosing treatment from the state of FIG. 23.

The operator then presses a staple (not illustrated in FIG. 23) from a staple inserting hole 172c of the stapling portion 172 by operating the control section 10 (refer to FIG. 1) of the inserting portion 169. As a result, a distal end portion of the extruded staple 21 is pressed into a recess portion (not shown) of the anvil arm 155, piercing and stapling the stomach wall and the small intestine wall (refer to FIG. 23). Thereafter, a cutter member 172e is displayed from a cutter member inserting hole 172d of the stapling portion 172, and a stapled inner peripheral side thereof is cut in a ring-like shape and an anastomosed hole 173 is formed as shown in FIG. 24.

The third embodiment enables easy insertion of the anvil 150 into the lumen and enables realizing a large diameter stapling, which enhances the handling operability.

Further according to the third embodiment, positional relationship between the stapling portion 172 and the anvil 150 can be precisely set during stapling. Further, by enabling adjusting the positional relationship between the stapling portion 172 and the anvil 150 by twisting the endoscope 7 and the anvil grasping piece 170, the stapling portion 172 and the anvil 150 can be grasped more conveniently, easily and accurately.

Figure 25:
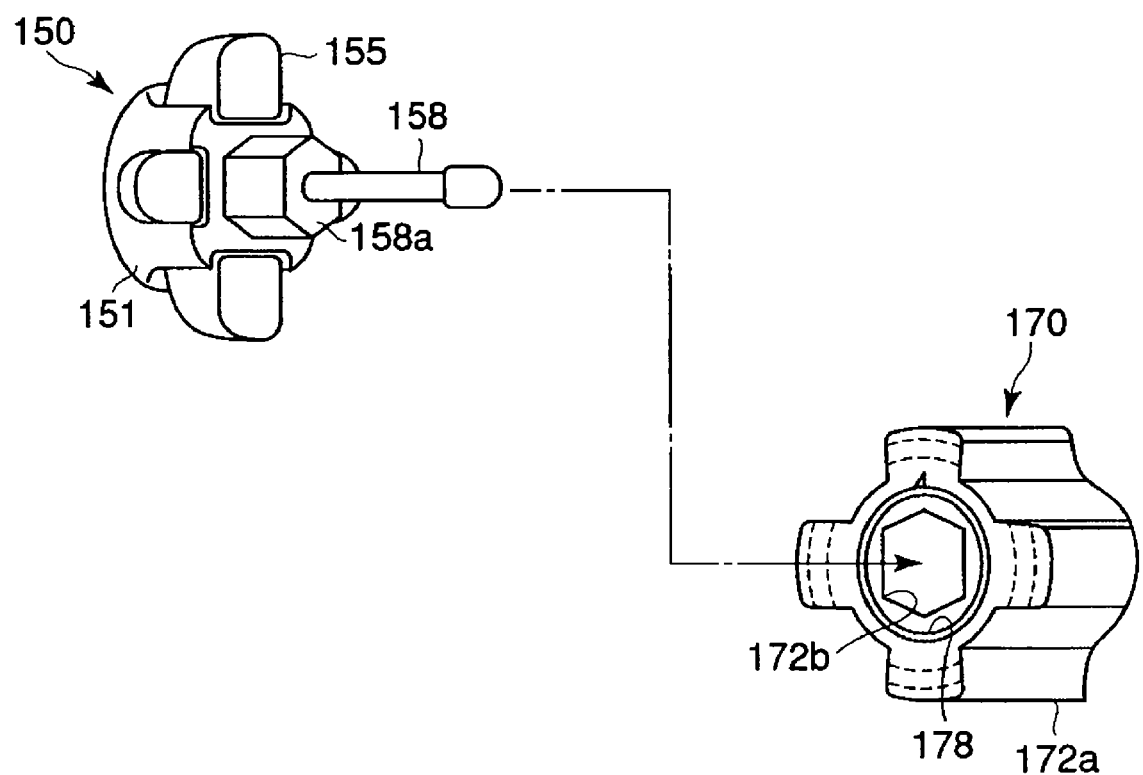
FIG. 25 is a view showing other example of an anvil used in a tissue stapler according to a third embodiment of the invention.

Further, the structure of the anvil is not limited as described above, at it can also take the form shown by FIG. 25. In FIG. 25, portions previously described with reference to FIG. 19 through FIG. 24 bear the same reference numerals and a detailed explanation thereof will be omitted.

In FIG. 25, a root end of the shaft member 158 of the anvil main body 151 includes a projecting fitting portion 158a substantially hexagonally shaped. Further, the anvil structure includes a complementary recess fitting portion 172b also hexagonally shaped and formed on a distal end side of the endoscope inserting tube path 178 in the stapling portion 172 of the inserting portion 169. The anvil 150 is fixedly grasped to fit the recess fitting portion 158a of the anvil main body 151 to the recess fitting portion 172b. Thereby, the positional relationship between the anvil 150 and the stapling portion 172 is accurately set to fix and obtain further improved, excellent effects.

Figure 26:
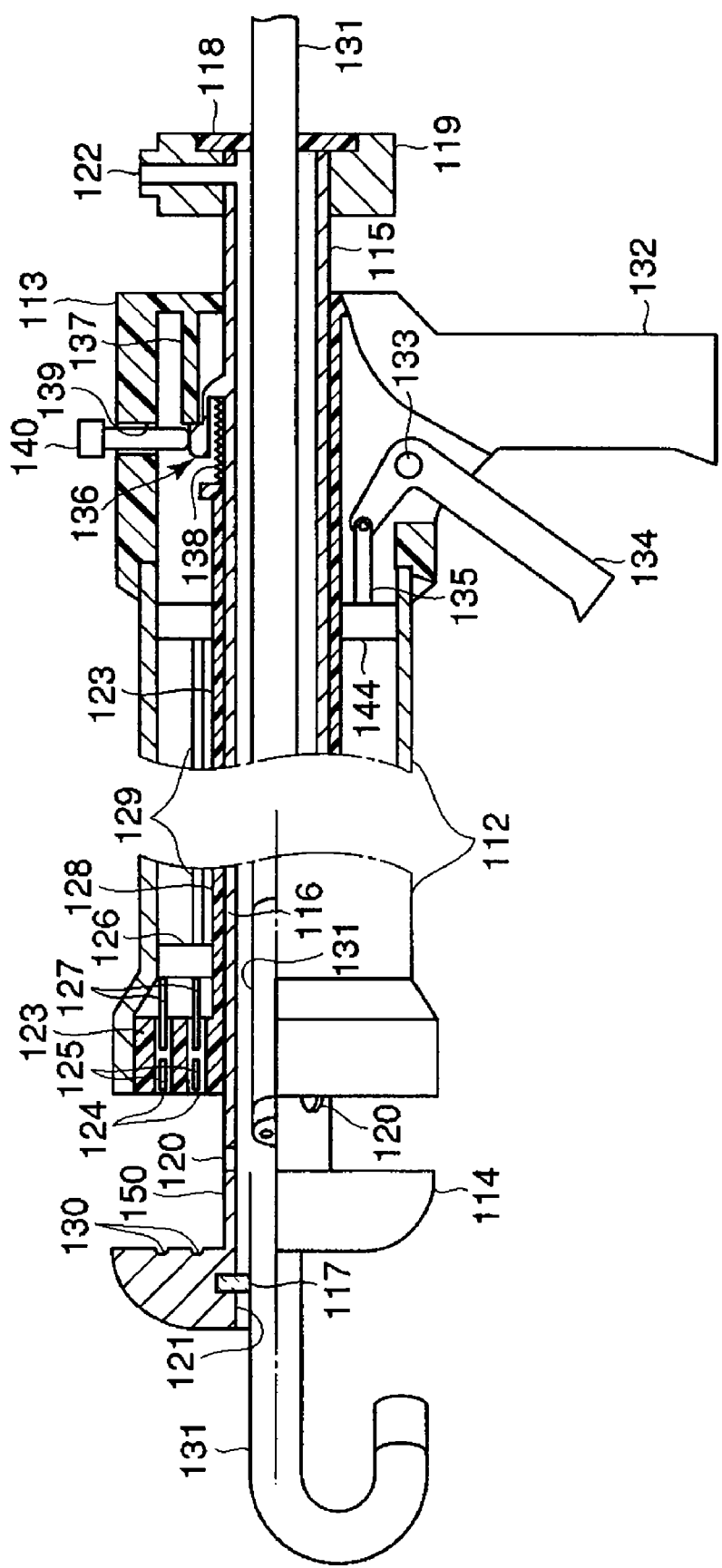
FIG. 26 is a view showing a reference example of a tissue stapler according to the invention.

Next, a fourth embodiment of a tissue stapler is now described by reference to FIG. 26, which shows a tissue stapler which includes an inserting portion 112 to be inserted into substantially flexible tissue, a stapling portion 111 provided on a distal end side of the inserting portion, an operating portion 113 provided on a proximal side of the inserting portion, and an anvil portion 114 arranged on a distal end of the stapling portion 111.

An operating shaft 115 extends on a proximal side of the anvil portion 114. The operating shaft 115 is arranged to move forward and rearward in an operating shaft inserting tube path 116 to communicate the stapling portion 111, the inserting portion 112, and the operating portion 113 from a distal end to a proximal side thereof. The proximal side projects from the operating portion 13, and a grasping portion 119 is provided at an end portion on the proximal side.

Further, the anvil portion 114 is provided with an endoscope inserting tube path 121 opened to a distal end side thereof, and communicating to the proximal side and to the operating shaft 115. An endoscope 131 is operably insertable through the endoscope inserting tube path 121. The endoscope inserting tube path 121 is provided with airtight valves 117, 118 on the distal end side and the proximal side to provide a predetermined interval therebetween. Further, the operating shaft 115 is provided with a plurality of suction holes 120 at a side wall portion, between the anvil portion 114 and the stapling portion 111, in a manner extending to a distal end side and an end portion on the proximal side, with a suction mouthpiece 122 communicating with the endoscope inserting tube 121. The suction mouthpiece 122 is connected with a suction source (not shown) to provide suction inside the operating shaft via the suction source.

The stapling portion 111 is substantially cylindrical at a distal end side thereof and includes the operating shaft inserting tube path 116 on a proximal side thereof. Further, the operating shaft inserting tube path 116 is inserted with the operating shaft 115.

Further, the stapling portion 111 includes a staple container 123 with a tube member extending to the proximal operating portion 113. A distal end of the staple container 123 is provided with a plurality of staple containing holes 124 in double rows substantially in a ring-like shape to penetrate the staple container 123. Staples 125 are respectively contained in the staple containing holes 124.

A proximal side of the staple container 123 has a cylindrical, moving member 126 that is movable forward and rearward, axially within the operating shaft inserting tube path 116. A distal face of the moving member 126 is arranged with staple extruding members 127, each substantially in a shape of a thin plate, at positions opposed to the staple containing holes 124. Further, at a wall face of a proximal side of the moving member 126, an extruding member 129, communicating from a distal end to a proximal side of the inserting portion 112, extends to the proximal side operating portion 113. The extruding member 129 is arranged movably in an inserting tube path 128, outwardly mounted to the operating shaft 115.

Further, an end face on a proximal side of the anvil portion 114 has recess portions 130 at positions opposed to the staple containing holes 124.

The operating portion 113 projects to provide a grip member 132 for grasping, a portion of a root of the grip member 132 being provided with a handle member 134 able to be operated to pivot centering on a shaft 133. The handle member 134 is coupled with an operating ring 144 via a link 135. The operating ring 144 is arranged to move forward and rearward coaxially within the operating shaft inserting tube path 116 and is attached to the extruding member 129.

Further, inside the operating portion 113 there is a projecting portion 137 of a rod-like shape, projecting from the proximal side to an inner side. The projecting portion 137 is opposed to an elastically deformable cantilever spring member 136 provided at a side portion of the operating shaft 115 and is selectively elastically lockable by the cantilever spring member 136. Further, a spring member 138 is engagingly attached between the projected portion 137 of the operating shaft 115 and the staple container 123.

Further, the operating portion 113 is provided with a switch hole 139 which is juxtaposed to the cantilever spring member 136, and the switch hole 139 is provided with a pressable switch 140. The switch 140 which is juxtaposed to the cantilever spring member 136 of the operating shaft 115, presses the cantilever spring member 136 by pressing the switch 40 and releases the operating portion 113 from being locked by the projecting portion 137. Thereby, the operating shaft 115 is biased to move to a proximal side by a biasing force of the spring member 138.

The above-described embodiment describes a tissue stapler suitable for the so-to-called regurgitant esophagitis used for forming a valve structure at, for example, a stomach-esophagus bonding portion 143 which staples the tissue at the cardia.

Thus, the operator inserts the stapling portion 111 of the inserting portion 112 including the anvil portion 114 orally to the stomach-esophagus bonding portion 143 under a field of view of the endoscope 131 inserted into the operating shaft 115. Next, the operator extrudes the operating shaft 115 projecting from the operating portion 113 against the spring member 138. Then, the anvil portion 114 is projected from the stapling portion 111 to the distal end side and forms a space as shown by a section of FIG. 26 between the anvil portion 114 and the distal end face of the stapling portion 111. At this point, the cantilever spring member 136 is brought into contact with the projected portion 137 of the operating shaft 115 and presses the switch 140 outside of the operating portion 113 by a distal end portion thereof. At this point, the operator adjusts the space at a pertinent position of the stomach-esophagus bonding portion 143 by adjusting the position of the anvil portion 114 by reversely rotating the endoscope 131 inserted into the stomach 141.

Figure 27:
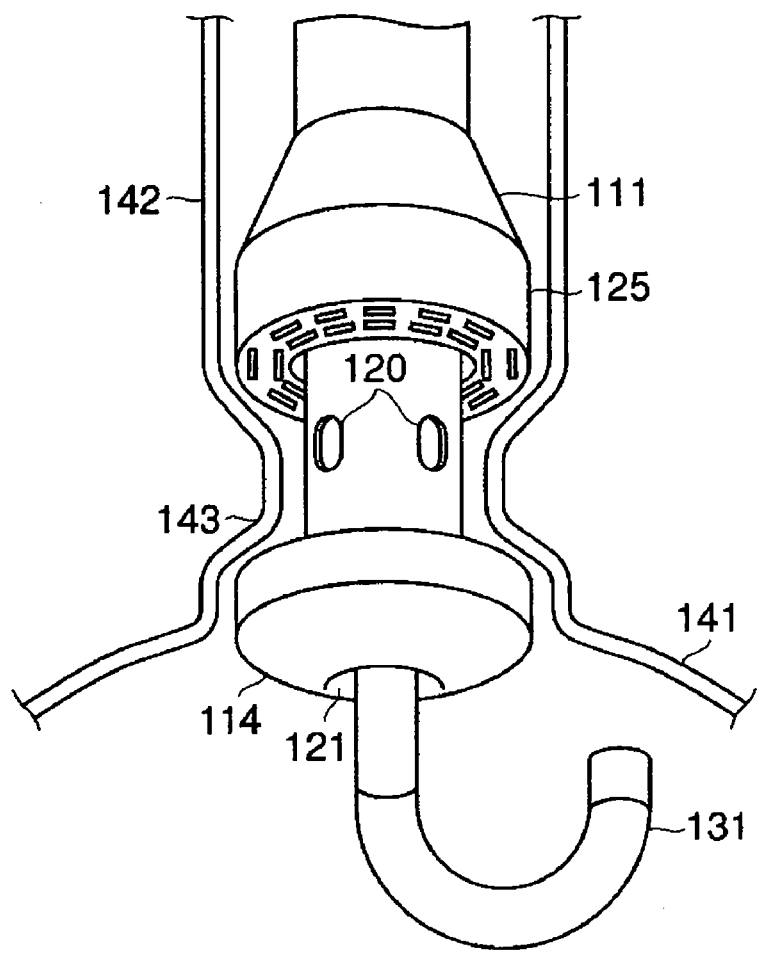
FIG. 27 is a view showing a state of the tissue stapler of FIG. 26 before stapling the tissue.

Subsequently, the operator actuates the suction source (not shown) connected to the suction mouthpiece 122 provided at the grasping portion 119 of the operating shaft 115, to provide suction inside of the operating shaft 115, and the esophagus 142 is drawn into the space between the anvil portion 114 and the stapling portion 111 (refer to FIG. 27). The switch 140 of the operating portion is then pressed, and the operating shaft 115 is moved and pressed back in the direction of the proximal side by the biasing force of the spring member 138. The esophagus 142 is pinched between the anvil portion 114 and the stapling portion 111.

Figure 28:
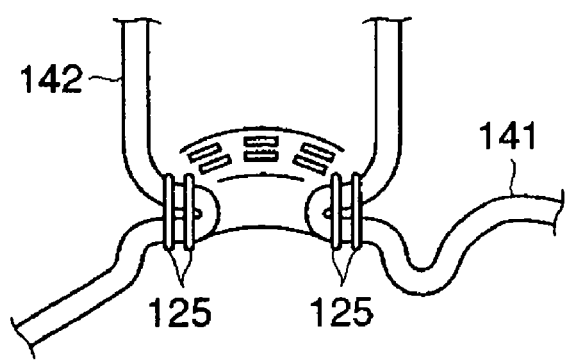
FIG. 28 is a view showing a state of finishing to staple the tissue of FIG. 27.

Next, the handle 134 is gripped and the operating ring 144 is moved in the direction of the distal end side. The extruding member 129, the moving member 126 and the staple extruding member 127 then move in the direction of the distal end side. At this stage, the staple extruding member 127 projects the staple 125 from the staple containing hole 127, whereby the distal end portion of the staple 125 pierces through the esophagus 142, and contacts the recess portion 130 of the anvil portion 114. The distal end is folded to bend to the inner side to staple the esophagus over an entire periphery thereof (refer to FIG. 28).

The fourth embodiment enables stapling the esophagus-stomach bonding portion over the entire periphery, orally and in one motion. A desired valve can thereby be easily formed at the stomach-esophagus bonding portion and, therefore, a highly effective treatment against regurgitant esophagitis is obtained. Further, by executing stapling with position confirmation using the field of view of the endoscope, convenient, easy and positive treatment can be realized.

Figure 29:
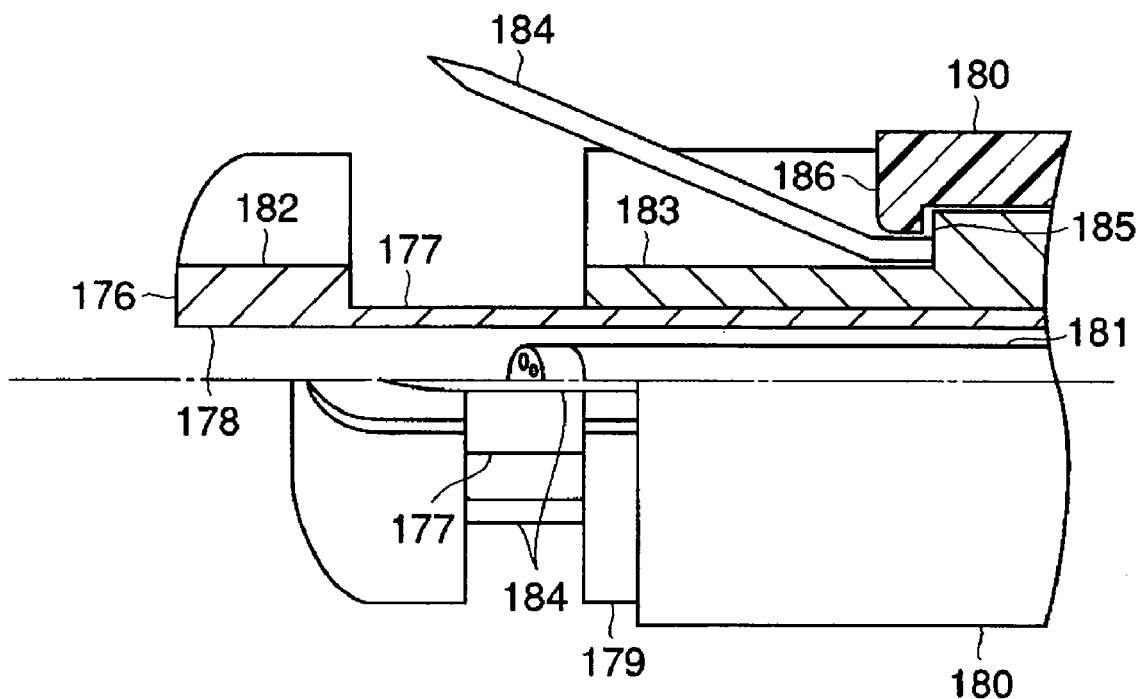
FIG. 29 is a view showing another reference example of a tissue stapler according to the invention.

FIG. 29 shows a tissue stapler according to a fifth embodiment, in which an anvil member 176 provided at a distal end side projects within an operating shaft member 177 on a proximal side thereof. The anvil member 176 and the operating shaft member 177 are formed with an endoscope inserting tube path 178 from a distal end side to reach a proximal side. A stapler main body 179 is outwardly mounted to the operating shaft 177 to move axially forward and rearward, and a staple pressing member 180 is inserted to an outer peripheral portion of the stapler main body 179 to move forward and rearward. The endoscope inserting tube path 178 is inserted with an endoscope 181 and a proximal side thereof is provided with a proximal side operating portion, not illustrated.

Figure 30:
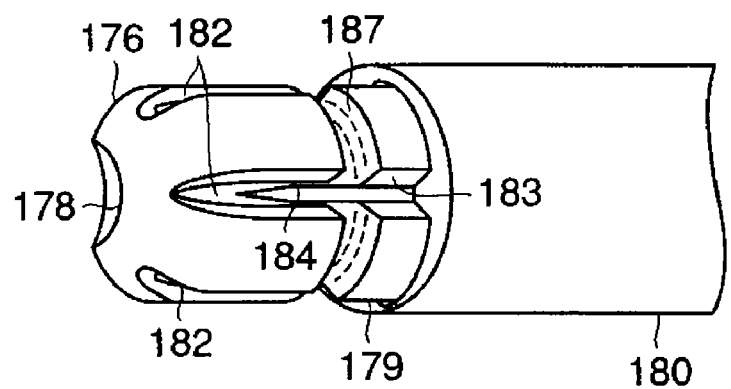
FIG. 30 is a view showing a state of restraining a staple member of FIG. 29.

An outer peripheral wall of the anvil member 176 is provided with a plurality of slit portions 182 in a long axis direction (distal and rear direction) with predetermined intervals therebetween (refer to FIG. 30). Further, a distal end side of the stapler main body 179 is provided with a plurality of locking staple containing slit portions 183 opposed to the slit portions 182 at predetermined intervals therebetween. The locking staple containing slit portions 183 are fixed to contain end portions of proximal sides of locking staple members 184 at fixing positions 185 at distal end portions on the proximal sides.

The locking staple members 184, on the proximal distal ends thereof are formed with an angle of inclination to open to an outer side directions of the stapler main body 179. The staple distal end portions thereof are arranged to be opened to the outer sides of a distal end portion of the stapler main body 179 and a peripheral wall of the stapler main body 179. Further, a distal end side of the staple pressing member 180 is provided with a plurality of restraining projections 186 contained in the slit portions 182 and the locking staple containing slit portion 183 are able to move forward and rearward and are placed at predetermined intervals.

Further, a distal end portion of the stapler main body 179 is provided with a plurality of staple containing holes 187 between the locking staple containing slits 183 in correspondence with recess portions designed to bend staples, not illustrated, formed at a side face of the anvil member 176 on the proximal side.

In the above-described embodiment, the operator first brings the anvil member 176 substantially into contact with the stapler main body 179 by acting to draw the operating shaft member 177 and moves the staple pressing member 180 in the direction of the distal end side. Then, the restraining projections 186 of the staple pressing member 180 press the locking staple members 184 to be contained in the slit portions 182 of the anvil member 176.

In this state, the endoscope 181 is inserted through the endoscope inserting tube path 178, the whole device being orally inserted to the esophagus-stomach stapling portion 189 along the endoscope 181. Successively, the operator forms a space between the anvil member 176 and the distal end portion of the stapler main body 179 as shown by a section in FIG. 29 by projecting the operating shaft member 177 while viewing the endoscope 181 in the stomach. At this stage, when the operator draws back the staple pressing member 180 to the proximal side, the locking staple members 184 are projected to the outer peripheral side of the staple pressing member 180.

Figure 31:
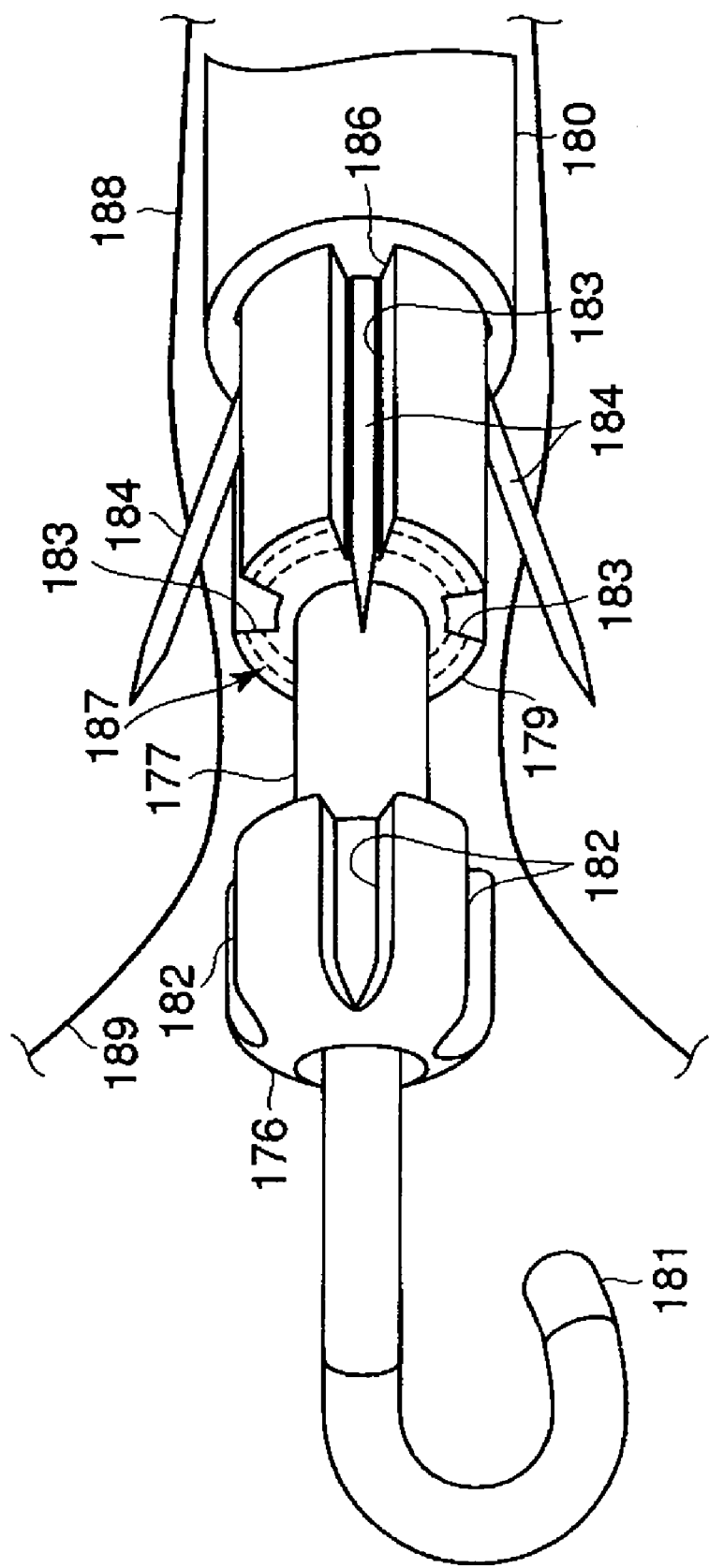
FIG. 31 is a view that explains a procedure of stapling the tissue of FIG. 29.

In this state, as the whole device is pressed to move forward orally, the locking staple members 184 pierce the muscle layer of the esophagus 188 (refer to FIG. 31), and subsequently, the staple pressing member 180 is pressed forward to the stapler main body 179. Then, by bringing the restraining projection 186 of the staple pressing member 180 into contact with the locking staple members 184 to move to the distal end side, the locking staple members 184 are contained in the locking staple containing slit portions 183 again. Thereby, the esophagus 188 is drawn into the space formed between the anvil member 176 and the distal end of the stapler main body 179. By drawing the operating shaft member 177 in this state, the esophagus 188 is pinched between the anvil member 176 and the distal end of the stapler main body 179 and by the subsequent operation of a control section, not illustrated, the esophagus tissue is stapled substantially over an entire periphery thereof by staples (not shown) arranged in the stapler main body 179.

According to the fifth embodiment, the esophagus tissue is mechanically drawn by the locking staple member 184 in a manner that enables forming the valve structure at the esophagus-stomach bonding portion by stapling the esophagus tissue over an entire periphery through all the layers including the muscle layer. Thus, a sturdier and longer lasting valve can be provided.

The above-described embodiments describe the case where the tissue is stapled over the entire periphery. The embodiments are, however, not so limited. For example, the position to be stapled can also be the portion of the esophagus-stomach bonding portion, such as a third periphery of or a half periphery thereof. Thereby, for a patient with a comparatively insignificant condition, the valve structure can be formed over less than the entire periphery. This is done by reducing a number and the outer diameter of the locking staple members used for drawing down the stapled portion, the anvil and the esophagus tissue by correspondingly limiting the stapled portion. Thus, an outer diameter of the inserting portion of the tissue stapler can be reduced and the burden on the patient whose tissue is being stapled can be alleviated. While there has been shown and described what are considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for stapling using a tissue stapler which includes: an inserting portion provided with an endoscope inserting tube path; a stapling portion provided with a staple injecting portion arranged at a distal end of the inserting portion; a staple receiving member detachably coupled to the inserting portion and being formed to bend a distal end portion of a stapling staple member pressed out from the staple injecting portion of the stapling portion and penetrating through the tissue; and a position information transmitting member provided at the staple receiving member for transmitting position information of the staple receiving member, wherein the staple receiving member comprises a shaft member structured to be grasped by and fixed to a treatment tool introduced through the inserting portion in a state of being opposed to the stapling portion via a body tissue, wherein the shaft member includes the position information transmitting member thereon, the method comprising the steps of:
inserting the staple receiving member provided with the position information transmitting member into a living body, in a manner such that the staple receiving member is separated from the inserting portion and the position information transmitting member provided at the staple receiving member is separated from the inserting portion;
inserting the inserting portion provided with the stapling portion into the living body; and
stapling the body tissue with the stapling portion and the staple receiving member after confirming the position of the staple receiving member based on position information transmitted from the position information transmitting member and penetrated through a wall in the living body.

2. The method according to claim 1, including:
detecting a position of the staple receiving member with a position detecting member receiving the position information from the position information transmitting member; and
guiding the staple receiving member based on detected information of the position detecting member with a guiding member.

3. The method according to claim 2, wherein the position detecting member comprises at least one of an endoscope introduced into the tissue stapler via the inserting portion and the treatment tool, and
wherein the guiding member comprises the treatment tool introduced into the guiding member via the inserting portion or the endoscope.

4. The method according to claim 2, wherein at least one of the position detecting member and the guiding member includes an endoscope and the treatment tool introduced transabdominally.

5. The method according to claim 1, wherein the staple receiving member is structured to be grasped by and fixed to the treatment portion using a magnetic force.

6. The method according to claim 1, including cutting an inner peripheral portion of the staple injecting portion with a cutting member.

7. The method according to claim 1, wherein the staple receiving member includes a main body thereof provided with a grasped portion having a diameter smaller than that of the stapling portion, a plurality of arm portions coupled with the main body and structured to be able to be folded in an inactivated state, and to expand when grasped at the grasped portion, to positions juxtaposed to the stapling portion.

8. The method according to claim 1, wherein the stapling portion is provided with a plurality of the staple injecting portions arranged in a substantially ring shape.

9. The method according to claim 1, including outputting electromagnetic waves for informing the position of the staple receiving member.

10. The method according to claim 9, including outputting light as the electromagnetic waves.

11. The method according to claim 1, wherein the stapling portion comprises a grasping piece made of first and second pivotably arranged arms which are openable and closeable to grasp the staple receiving member.

12. The method according to claim 1, including rotating a portion of the stapling portion relative to the staple receiving member with a rotating member.

13. The method according to claim 1, wherein the stapling portion comprises staples that are peripherally and spacedly arranged relative to one another and the staple members being oriented at an angle relative to the axial direction of the stapling portion.

14. The method according to claim 1, further comprising a step of inserting a guide wire into the living body before inserting the staple receiving member into the living body, the staple receiving member being inserted following the guide of the guide wire.

15. The method according to claim 1, wherein the position information transmitting member provided at the staple receiving member and the inserting portion are located such that a living tissue is provided between the position information transmitting member and the inserting portion.

16. A method for stapling using a tissue stapler which includes: an inserting portion provided with an endoscope inserting tube path; a stapling portion provided with a staple injecting portion arranged at a distal end of the inserting portion; a staple receiving member detachably coupled to the inserting portion and being formed to bend a distal end portion of a stapling staple member pressed out from the staple injecting portion of the stapling portion and penetrating through the tissue; and a position information transmitting member provided at the staple receiving member for transmitting position information of the staple receiving member, wherein the staple receiving member comprises a shaft member structured to be grasped by and fixed to a treatment tool introduced through the inserting portion in a state of being opposed to the stapling portion via a body tissue, wherein the shaft member includes the position information transmitting member thereon, the method comprising the steps of:

inserting the staple receiving member provided with the position information transmitting member into a living body, in a manner such that the staple receiving member is separated from the inserting portion;

inserting the inserting portion provided with the stapling portion into the living body; and stapling the body tissue with the stapling portion and the staple receiving member after confirming the position of the staple receiving member based on position information transmitted from the position information transmitting member and penetrated through a wall in the living body, including using a suction arrangement to create suction in an area between the stapling portion and the staple receiving member to draw the body tissue therebetween for being thereafter clamped and stapled.

* * * * *